United States Patent
Clarion et al.

(10) Patent No.: US 10,800,806 B2
(45) Date of Patent: Oct. 13, 2020

(54) STEROL DERIVATIVES AND USE THEREOF FOR TREATING DISEASES INVOLVING TRANSFORMED ASTROCYTE CELLS OR FOR TREATING MALIGNANT HAEMOPATHIES

(71) Applicant: BETA INNOV, Paris (FR)

(72) Inventors: Ludovic Clarion, Saint Gely du Fesc (FR); Marcel Mersel, Montpellier (FR); Didier Petite, Montpellier (FR)

(73) Assignee: BETA INNOV, Paris (FR)

( * ) Notice: Subject to any disclaimer, the term of this patent is extended or adjusted under 35 U.S.C. 154(b) by 244 days.

(21) Appl. No.: 14/399,336

(22) PCT Filed: May 7, 2013

(86) PCT No.: PCT/IB2013/053669
§ 371 (c)(1),
(2) Date: Nov. 6, 2014

(87) PCT Pub. No.: WO2013/168096
PCT Pub. Date: Nov. 14, 2013

(65) Prior Publication Data
US 2015/0086615 A1    Mar. 26, 2015

Related U.S. Application Data

(60) Provisional application No. 61/656,151, filed on Jun. 6, 2012.

(30) Foreign Application Priority Data

May 10, 2012   (FR) .................................. 12 305518

(51) Int. Cl.
| | |
|---|---|
| *C07J 9/00* | (2006.01) |
| *A61K 31/575* | (2006.01) |
| *A61K 31/58* | (2006.01) |
| *C07J 17/00* | (2006.01) |
| *C07J 41/00* | (2006.01) |

(52) U.S. Cl.
CPC ............ *C07J 9/005* (2013.01); *A61K 31/575* (2013.01); *A61K 31/58* (2013.01); *C07J 9/00* (2013.01); *C07J 17/00* (2013.01); *C07J 41/0055* (2013.01)

(58) Field of Classification Search
CPC ................................... C07J 9/00; C07J 9/005
See application file for complete search history.

(56) References Cited

FOREIGN PATENT DOCUMENTS

WO     WO 97/45440    * 12/1997

OTHER PUBLICATIONS

Fieser et al., "alpha"—Spinasterol, Journal of the American Chemical Society, vol. 71, pp. 2226-2230, 1949 (Abstract attached).*
Reckewell et al., In vitro study of hte cytotoxicity and selectivity of 7beta-hydroxycholesterol, Arzneimittel-Forschung, 37(2), pp. 139-141, 1987 (Abstract attached).*
Won Hyun et al., Effects of combinations of 7beta-hydroxycholesterol and anticancer drugs or ionizing radiation on the proliferation of cultured tumor cells, Anticancer Research, 22(2A), pp. 943-948, 2002 (Abstract attached).*
Vig et al., "Amino acids as promoieties in prodrug design and development." Advanced Drug Delivery Reviews, vol. 65 (2013) 1370-1385. Available online Oct. 22, 2012.*
Werthle Myriam et al.: "Local administration of 7-beta-hydroxycholesteryl-3-oleate inhibits growth of experimental rat C6 glioblastoma", Cancer Research, American Association for Cancer Research, US, vol. 54, No. 4, Feb. 15, 1994 (Feb. 15, 1994), pp. 998-1003, XP002619892, ISSN: 0008-5472 cited in the application the whole document.
Kimura M et al.: "The Reactions of Cholesteryl Acetate With Tert-Butyl Hydroperoxide and Molybdenum Complexes", Chemical and Pharmaceutical Bulletin, Pharmaceutical Society of Japan. JP, vol. 29. No. 1. Jan. 1, 1981 (Jan. 1, 1981). pp. 35-42, XP002069568, ISSN: 0009-2363 p. 39; compound 5.
Louis F. Fieser et al.: Journal of the American Chemical Society, vol. 74. No. 13, Jul. 5, 1952 (Jul. 5, 1952), pp. 3309-3313. XP055072731, ISSN: 0002-7863. DOI: 10.1021/jaOI133a027 p. 3313. col. 2.
Dugas D et al.: "Synthesis of 7-dehydrocholesterol through a palladium catalyzed selective homoannular conjugated diene formation", Journal of Molecular Catalysis A: Chemical. Elsevier. Amsterdam. NL, vol. 253. No. 1-2, Jul. 1, 2006 (Jul. 1, 2006). pp. 119-122, XP028015706, ISSN: 1381-1169. DOI: 10.1016/J, MOLCATA.2006.03.014 [retrieved on Jul. 1, 2006] p. 120; compounds 3, 5b.
Jia Xian et al.: "Studies on the synthesis and antitumor activities of oxysterol derivatives", Zhongguo Yaowu Huaxue Zazhi—Chinese Journal of Medicinal Chemistry. Gai-Kai Bianjibu. Shenyang. CN, vol. 15. No. 1, Jan. 1, 2005 (Jan. 1, 2005). pp. 12-15, XP001539990, ISSN: 1005-0108 compound 12 abstract, English Abstract.
C. W. Shoppee et al: "Steroids. Part xxx. Some properties of the cholest-5-ene-3β7ε-diols and their esters", Journal of the Chemical Society C: Organic, Jan. 1, 1968 (Jan. 1, 1968). pp. 981, XP055072319, ISSN: 0022-4952. DOI: 10.1039/j39680000981 p. 981. col. 2.
Selye H: "Correlations Between the Chemical Structure and the Phamacological Actions of the Steroids", Endocrinology, the Endocrine Society, US, vol. 30, Jan. 1, 1942 (Jan. 1, 1942), pp. 437-453, XP000974346, ISSN: 0013-7227 7alpha-hydroxycholesterol dibenzoate; p. 444.

(Continued)

Primary Examiner — Barbara P Badio
(74) Attorney, Agent, or Firm — Nixon & Vanderhye

(57) ABSTRACT

Novel sterol derivatives, the preparation method thereof, pharmaceutical compositions containing them and use thereof for treating diseases involving transformed astrocyte cells or for treating malignant haemopathies. The treatment of glioblastoma multiforme, as well as of other cancers, such as lymphomas, neuroblastomas and melanomas is also described.

35 Claims, 14 Drawing Sheets

(56) References Cited

OTHER PUBLICATIONS

International Search Report, dated Aug. 2, 2013, from corresponding PCT application.

Jia Xian et al. "Studies on the synthesis and antitumor activities of oxysterol derivatives." Zhongguo Yaowu Huaxue Zazhi—Chinese Journal of Medicinal Chemistry. Gai-Kai Bianjibu. Shenyang. CN, vol. 15. No. 1, Jan. 1, 2005 (Jan. 1, 2005). pp. 12-15, XP001539990, ISSN: 1005-0108 compound 12 abstract.

Henbest, H. B., and E. R. H. Jones. "363. Studies in the sterol group. Part L. 7-substituted cholesterol derivatives and their stereochemistry (part III). 7-alkoxycholesterol derivatives." Journal of the Chemical Society (Resumed), 1948, pp. 1798-1803.

Harada, N. et al. "The benzoate sector rule, a method for determining the absolute configurations of cyclic secondary alcohols." Journal of the American Chemical Society 90.26, 1968, pp. 7349-7351.

\* cited by examiner

| Duration of treatment | Control | 1.b 22µM (liposome form) | 2.b 22µM (liposome form) |
|---|---|---|---|
| 7 days | A | C | E |
| 28 days | B | D | |

Fig. 13

STEROL DERIVATIVES AND USE THEREOF FOR TREATING DISEASES INVOLVING TRANSFORMED ASTROCYTE CELLS OR FOR TREATING MALIGNANT HAEMOPATHIES

FIELD OF THE INVENTION

The invention relates to novel sterol derivatives, the preparation method thereof, the pharmaceutical compositions containing them and use thereof for treating diseases involving astrocyte cells transformed into cancer cells, and in particular for treating glioblastoma multiforme, or for treating malignant haemopathies, in particular involving transformed myeloid cells, or for treating lymphomas.

BACKGROUND OF THE INVENTION

Cellular transformation corresponds to the transition from a normal eukaryotic cell to an immortalized cell and/or a cancerous eukaryotic cell. The terms "transformed cell" or "cancer cell" will be used synonymously hereinafter.

Glioblastoma multiforme (GBM), also known as grade IV astrocytoma, is a brain tumour characterized by transformation of astrocyte cells into cancer cells, in particular passing through gliomas of grade I, grade II and grade III.

Despite the substantial scientific and therapeutic advances in the area of oncology, GBM is still an incurable cancer. At best, researchers and doctors are satisfied when the median life of patients can be prolonged by some months, at most fifteen months.

One of the problems encountered in the treatment of GBM is relapse caused by stem cells. In fact, even when the existing therapies succeed in eradicating most of the tumour, the stem cells often cause the development of a new tumour (1,2).

Current therapies always consist of resection of the tumour, if its location allows this, followed by radiotherapy and/or chemotherapy as appropriate. In chemotherapy, one of the leading treatments is bitherapy, which consists of administering Avastin (inhibition of binding of VEGF to its receptors) and irinotecan (inhibitor of topoisomerase I). Tritherapy of the PCV type, which is a combination of procarbazine (DNA alkylating agent), lomustine (CCNU; nonspecific alkylating agent) and vincristine (inhibition of microtubule polymerization) is at present very controversial. Temozolomide, a guanine alkylating agent, in combination with radiotherapy, shows an increase in median survival especially for patients with hypermethylated DNA. Clinical trials (phase III), testing cilengitide (inhibition of some integrin receptors) and talampanel (blocking of glutamate channels of the AMPA type), are in progress.

Immunotherapy studies and clinical trials are of two types:
- adaptive immunotherapy, in which cells activated in vitro are injected into the patient, such as lymphokine-activated killer cells (LAK; phase II clinical trials) or cytotoxic T lymphocytes (CTL; phase I clinical trials) injected intracranially. At present, observations show a survival of 20 months, which is very marginal.
- active immunotherapy, which consists of using vaccines (phase I) and dendritic cells (phase II). This does not show a significant improvement in patient survival. These trials have been halted.

Gene therapies, which consist of using adenoviruses, retroviruses or measles viruses as vectors of molecules with anti-cancer potential, show an improvement in survival of only 6 to 11 months. Cell therapy that proposes the use of neuronal stem cells as transporters of medicaments in GBMs is still at the demonstration stage in basic research.

An approach that has been somewhat neglected in recent decades, and is again envisaged, consists of action at the level of glycolysis and oxidative phosphorylation. Cancer cells increase their consumption of glucose because they tend to modify their metabolism towards anaerobic metabolism, even if oxygen supply is not a limiting factor. This phenomenon, observed by Warburg (3), is due to overexpression of HF (Hypoxia Induced Factor) and of the Myc pro-oncogene. HIF increases the conversion of pyruvate to lactate, anaerobically, by inactivating pyruvate dehydrogenase, which is a key enzyme in aerobic respiration. Myc stimulates the biosynthesis of glutamine, which is involved in anaerobic respiration (4).

In this context, clinical trials acting on energy metabolism are in progress. There may be mentioned, as examples (4):
- metformin: inhibitor of mitochondrial respiratory complex I, which in its turn induces AMPK, which slows down cell proliferation;
- phoretine: agent for reducing glucose import;
- phenylacetate: agent for reducing the glutamine level;
- dichloroacetate: inhibitor of pyruvate dehydrogenase.

All these molecules, except dichloroacetate, are being tested (phase II clinical trials) and the observations are not yet known at present.

It has now been found that sterol derivatives targeting a specific aspect of the energy metabolism of astrocytes, the cell type at the origin of GBMs, could be used for treating glioblastoma multiforme.

SUMMARY OF THE INVENTION

The original aspect of the invention consists of using the particular energy metabolism of the astrocyte cell (of glial origin), the transformation of which ultimately leads to the formation of GBMs.

In fact, the astrocyte cell at the same time uses the supply of energy, in the form of ATP, via oxidative phosphorylation (Krebs cycle coupled to electron transport in the mitochondrion) and via the glycolysis: in the latter, pyruvate does not enter the Krebs cycle but is reduced to lactate by the enzyme lactate dehydrogenase (LDH) of type 5. In addition to ATP supply, the astrocyte uses glycolysis, via the production of lactate, to supply the adjacent cell, the neuron, with neurotransmitter (glutamate).

In the following table, the energy metabolism of the astrocyte, normal or cancerous, is compared schematically with that of other cells:

|  | Astrocytes | | Other cells | |
| --- | --- | --- | --- | --- |
|  | Mitochondrial respiration | Glycolysis | Mitochondrial respiration | Glycolysis |
| Normal cells | 50% | 50% | 90% | 10% |
| Cancer cells | GBM 1% | GBM 99% | 1% | 99% |

The energy metabolism of the astrocyte is special: in fact, mitochondrial respiration and glycolysis function in concert.

It is this specific metabolic duality of the normal astrocyte cell, namely mitochondrial respiration on the one hand, and glycolysis on the other hand, that forms the basis for the strategy of preparing the sterol derivatives according to the invention.

In fact, the inventors put forward the working hypothesis according to which the sterol derivatives according to the invention can orient the energy metabolism of cancerous astrocyte cells from glycolysis to mitochondrial respiration, a process that would lead to their death.

7β-Hydroxycholesterol (7β-OHCH), a molecule with high anti-cancer potential (5,6), shows remarkable cytotoxicity on immortalized (spontaneously transformed) rat astrocyte lines (7,8) and GBMs (rat line C6) "in vitro" (9). Studies demonstrate that esterification of 7β-OHCH at C3-OH by the intracellular fatty acids (formation of 7β-OHCH—C3-ester) was strongly implicated in the toxic effect of the parent molecule, 7β-OHCH (7, 8, 10).

However, the mechanism of action of 7β-OHCH, whether or not esterified at C3-OH, on GBMs "in vitro" was far from being elucidated. Recently, studies carried out on the C6 lines have shown that 7β-OHCH modulates the architecture and the dynamics of the rafts, microdomains in the plasma membrane, sites of initiation of certain cellular messengers including that of protein kinase Akt, a key enzyme in cellular energy metabolism (11). In fact, oxysterol, by disturbing the architecture of the rafts, would consequently affect the activity of Akt, particularly during the transformation of normal cells into cancer cells: Akt regulates the capture of glucose and the glycolysis activity in these cells.

Surprisingly, it has now been found that the sterol derivatives according to the invention, having a 7beta-hydroxycholesterol basic structure bearing substituents in position 3 and protective groups in position 7, would simultaneously permit inhibition of glycolysis, essential for the energy supply of the high-grade cancerous astrocyte and, at the same time, restore mitochondrial respiration, which is also "lethal" for this cell.

In fact, this dual action leads to "overheating" of the cancer cell, leading to its death.

Moreover, it has been shown that the sterol derivatives according to the invention also have activity with respect to stem cells, thus permitting total destruction of the glioblastoma cells.

The activity of the sterol derivatives according to the invention with respect to glioblastoma also means that their use can be envisaged in the treatment of malignant haemopathies of the myeloid type, owing to the similarity of the cell metabolism of the myeloid cell with that of the astrocyte; in the treatment of neuroblastomas, the neurons having the same embryological and cellular origin as the astrocyte; and in the treatment of melanomas, since the melanocytes have the same embryological origin as the astrocytes, as will be explained later.

Moreover, the fact that the myeloid line and the lymphoid line have a common origin, namely the pluripotent haematopoietic stem cell, means it is also possible to envisage the use of the sterol derivatives according to the invention for treating lymphomas.

BRIEF DESCRIPTION OF THE DRAWINGS

FIG. 8 shows treatment of GBM cells with molecule 2.a.

FIG. 13 shows the results (in photographs at magnification 10×10) of neuroblastomas treated with empty liposomes (controls) or with liposomes containing molecule 1.b or 2.b, 24 hours after starting the culture.

FIG. 14(B) shows the results of the addition of oxamate, in aqueous form (18 mM), or of molecule 2.b, in ethanolic form (36 mM), which inhibits the enzymatic activity of LDH LL almost completely and that of LDH G8M partially.

DETAILED DESCRIPTION OF THE INVENTION

Figure 1:
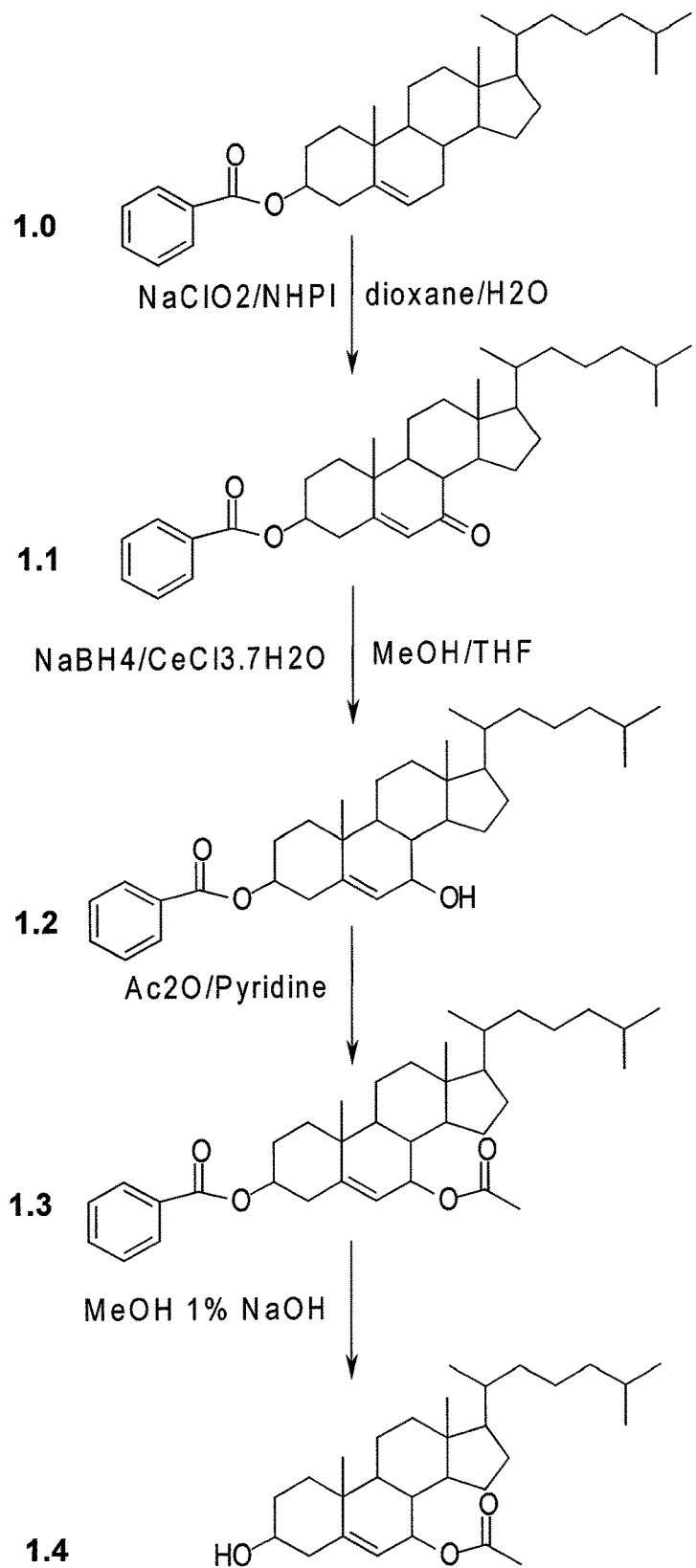
FIG. 1 shows the reaction diagram for the preparation of 7beta-acetylcholesterol (compound 1.4).

The invention therefore relates to compounds of formula (I)

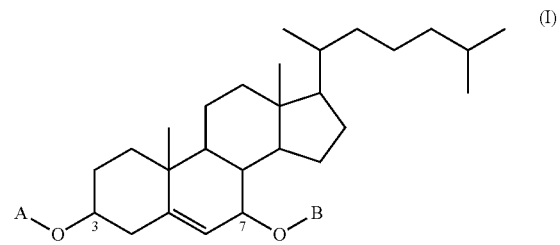

in which

A represents an —($R_1$)$_n$— group in which $R_1$ is an amino acid residue bound by its C-terminal end and n=1 or 2, each $R_1$ being identical or different, in which the N-terminal end of said amino acid can be substituted with a —C—(O)—$R_2$ group in which $R_2$ is a mono- or polycyclic $C_6$-$C_{14}$ arylalkyl group or with an $R_3$—C(O)—O— or $R_3$—C(O)— group in which $R_3$ is a $C_1$-$C_6$ alkyl which is unsubstituted or substituted with at least one group selected from OR, NHR and SR, where R represents hydrogen, a linear $C_1$-$C_{12}$ alkyl or an unsubstituted $C_6$-$C_{14}$ aryl; or $R_3$ is a $C_6$-$C_{14}$ aryl or $C_5$-$C_{14}$ heteroaryl group, which are unsubstituted or substituted with at least one linear or branched $C_1$-$C_6$ alkyl or with at least one group selected from OR, NHR and SR, as defined above; or a mono- or polycyclic $C_5$-$C_{14}$ heteroarylalkyl group that can comprise one or more heteroatoms, which may be identical or different, which is unsubstituted or substituted with at least one linear or branched $C_1$-$C_4$ alkyl; a mono- or polycyclic $C_6$-$C_{14}$ arylalkyloxy group or a mono- or polycyclic $C_5$-$C_{14}$ heteroarylalkyloxy group that can comprise one or more heteroatoms, which may be identical or different, which are unsubstituted or substituted with at least one linear or branched $C_1$-$C_4$ alkyl, or a —C(O)—NH—$R_4$ or —C(S)—NH—$R_4$ group in which $R_4$ is hydrogen; a $C_1$-$C_{12}$ alkyl group, linear or branched, unsubstituted or substituted with at least one group selected from OR, NHR and SR, as defined above; a $C_6$-$C_{14}$ aryl group, unsubstituted or substituted with at least one linear or branched $C_1$-$C_6$ alkyl or at least one group selected from OR, NHR and SR, as defined above; an acyl group; a formyl group; a sulphonyl group; a sulphinyl group; or else $R_4$ represents an allyl group or a sugar residue;

a —C(O)—$OR_5$ group in which $R_5$ is a $C_1$-$C_{12}$ alkyl, linear or branched, unsubstituted or substituted with at least one group selected from OR, NHR and SR, as defined above;

a —C(O)—$R_6$ group in which $R_6$ is a saturated $C_5$-$C_{14}$ heterocycle comprising 1 or 2 heteroatoms, unsubstituted or substituted with at least one linear or branched $C_1$-$C_6$ alkyl or at least one group selected from OR, NHR and SR, as defined above; or $R_6$ represents a linear or branched $C_1$-$C_{12}$ alkyl group unsubstituted or substituted with at least one group selected from OR, NHR and SR, as defined above; a $C_6$-$C_{14}$ aryl group or a $C_5$-$C_{14}$ heteroaryl group, which are unsubstituted or substituted with at least one linear or branched $C_1$-$C_6$ alkyl or with at least one group selected from OR, NHR and SR, as defined above; or else a sugar residue.

B represents a —C(O)—$R_7$ group in which $R_7$ is hydrogen; a $C_1$-$C_{12}$, preferably $C_1$-$C_6$, alkyl, linear or branched, unsubstituted or substituted with at least one group selected from OR, NHR and SR, as defined above; a $C_6$-$C_{14}$ aryl group, unsubstituted or substituted with at least one linear or branched $C_1$-$C_6$ alkyl or at least one group selected from OR, NHR and SR, as defined above; or $R_7$ represents $OR_8$, in which $R_8$ is a linear or branched, $C_1$-$C_{12}$, preferably $C_1$-$C_6$, alkyl.

The alkyl group denotes a linear or branched $C_1$-$C_{12}$ group such as the methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl, heptyl, octyl, nonyl, decyl, undecyl or dodecyl groups, the linear or branched $C_1$-$C_6$ alkyl groups being preferred.

The aryl group denotes an unsaturated, monocyclic or polycyclic, carbocyclic, $C_6$-$C_{14}$ group, such as the phenyl, naphthyl, indenyl, anthracenyl groups and more particularly the phenyl group.

The heteroaryl group denotes an unsaturated, monocyclic or polycyclic, $C_5$-$C_{14}$ group, comprising one or more heteroatoms, which may be identical or different, and more particularly a purine or pyrimidine base.

By "heteroatom" is meant an oxygen, nitrogen or sulphur atom.

By "sugar residue" is meant, for example, a unit of the glucose, ribose or arabinose type.

Advantageous amino acid residues are, for example, methionyl, glycinyl or alanyl units.

Preferred compounds of formula (I) are those in which at least one of the following conditions is fulfilled:

A represents an —$(R_1)_n$— group in which $R_1$ is an amino acid residue and n=1 or 2;

A represents an —$(R_1)_n$— group in which $R_1$ is an amino acid residue, n=1 or 2 and the N-terminal end of said amino acid is substituted with an arylalkoxycarbonyl group, in particular benzyloxycarbonyl; or with an $R_3$—C(O)—O— or $R_3$—C(O)— group in which $R_3$ is a $C_1$-$C_6$ alkyl, unsubstituted or substituted with at least one group selected from OR, NHR and SR, as defined above; or $R_3$ is a $C_6$-$C_{14}$ aryl or $C_5$-$C_{14}$ heteroaryl group, which are unsubstituted or substituted with at least one linear or branched $C_1$-$C_6$ alkyl, or with at least one group selected from OR, NHR and SR, as defined above;

A represents an alanyl radical linked to a glycinyl radical, optionally substituted on its N-terminal end with an arylalkoxycarbonyl group, in particular benzyloxycarbonyl;

A represents a methionyl radical linked to a glycinyl radical, optionally substituted on its N-terminal end with an arylalkoxycarbonyl group, in particular benzyloxycarbonyl;

A represents a —C(O)—$R_6$ group in which $R_6$ is a 2,2-dimethyl-1,3-dioxolane group, or a linear or branched $C_1$-$C_6$ alkyl group, unsubstituted or substituted with at least one group selected from OR, NHR and SR, as defined above; a $C_6$-$C_{14}$ aryl group or a $C_5$-$C_{14}$ heteroaryl group, which are unsubstituted or substituted with at least one linear or branched $C_1$-$C_6$ alkyl, or with at least one group selected from OR, NHR and SR, as defined above; or else a sugar residue.

Advantageously, B represents an acyl group in which the alkyl group is $C_1$-$C_6$, in particular acetyl or an alkoxycarbonyl group in which the alkyl group is $C_1$-$C_6$, in particular a tert-butoxycarbonyl group.

B can also, in particular, represent a $C_1$-$C_6$ alkyl group, unsubstituted or substituted with at least one group selected from OR, NHR and SR, as defined above; or a $C_6$-$C_{14}$ aryl group, unsubstituted or substituted with at least one linear or branched $C_1$-$C_6$ alkyl or with at least one group selected from OR, NHR and SR, as defined above.

Preferred compounds of formula (I) are as follows:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)acetamido)propanoate (molecule 1.a);

7-acetoxy-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl-2,2-dimethyl-1,3-dioxolane-4-carboxylate (molecule 2.a);

7-acetoxy-10,13-dimethyl-17-(6-methylheptan-2-yl)-2,3,4,7,8,9,10,11,12,13,14,15,16,17-tetradecahydro-1H-cyclopenta[a]phenanthren-3-yl-2,2-dimethyl-1,3-dioxolane-4-carboxylate (molecule 2.b).

The compounds of formula (I) can be obtained from cholesterol by a method comprising the following steps:

protection of the hydroxyl function in position 3 of cholesterol with a protective group, such as, for example, an acyloxy $R_9$—C(O)— group in which the $R_9$ group is a substituted or unsubstituted $C_1$-$C_6$ alkyl, or a substituted or unsubstituted aryl group, in particular an arylalkoxycarbonyl group, introduction of a ketone function in position 7, reduction of the ketone function to a hydroxyl function, introduction of a protective group on the hydroxyl function in position 7, corresponding to the B group, such as for example an acyl, aryl or alkoxycarbonyl group, or an acyloxy $R_{10}$—C(O) group in which $R_{10}$ is a substituted or unsubstituted $C_1$-$C_6$ alkyl, an aryl, unsubstituted or substituted with at least one linear or branched $C_1$-$C_6$ alkyl, or a $C_6$-$C_{14}$ heteroaryl, unsubstituted or substituted with at least one linear or branched $C_1$-$C_6$ alkyl or at least one group selected from OR, NHR and SR, as defined above, deprotection of the hydroxyl function in position 3.

After deprotection of the hydroxyl function in position 3, said hydroxyl function can be substituted with the desired A group.

The introduction of a ketone function in position 7 can be carried out by usual oxidation methods.

The reduction of the ketone function to a hydroxyl function, selectively in position β, can be carried out for example by Luche's method using $NaBH_4$ in the presence of cerium chloride heptahydrate (12).

The invention also relates to the pharmaceutical compositions or medicaments comprising at least one compound of formula (I) and a pharmaceutically acceptable vehicle.

The pharmaceutical composition according to the invention can consist of a liposomal preparation comprising at least one compound of formula (I). The liposomes can be produced by various techniques known to a person skilled in the art. Various lipids constituting the liposomes can be used [Medical Application of Liposomes (1986) edited by Kunio Yagi, Japan Scientific Societies Press, Tokyo, Karger].

Alternatively, said liposome can consist of a so-called "improved" liposome having a size distribution predominantly between 40 and 80 nm and with a composition that is stable over time or of a so-called "concentrated" liposome having the same size distribution but comprising a higher concentration of active molecule, in particular 50% higher than that of the "improved" liposome.

The "improved" liposome can be obtained by a preparation method comprising the following steps:

contacting the active molecule to be included in the liposome and the phospholipid in an organic solvent, evaporating the solvent under a nitrogen stream so as to obtain a lipid film, dissolving the lipid film in an organic solvent, evaporating said solvent under a nitrogen stream and taking up the lipid film in an aqueous buffer sonication in an ultrasonic bath, obtaining the vesicles by extrusion.

Preferably, sonication is carried out for 10 pulses of one min at a temperature of about 20° C. Extrusion can be carried out on a PVDF-type membrane having a pore size of 200 nm.

The "concentrated" liposomes can be obtained by a preparation method comprising the steps of:

contacting the active molecule to be included in the liposome and a quantity of phospholipid which is higher than the one used in the usual techniques, notably twice the usual quantity, in an organic solvent, evaporating the solvent under reduced pressure so as to obtain a lipid film, dissolving the lipid film in an organic solvent, evaporating said solvent under reduced pressure and taking up the lipid film in an aqueous buffer, sonication in an ultrasonic bath, obtaining the vesicles by extrusion.

Preferably, sonication is carried out for 20 pulses of one min at a temperature of about 20° C. Extrusion can be carried out on a PVDF-type membrane having a pore size of 200 nm.

Preferably, evaporation is carried out at a pressure below about 3 kPa (30 mbar) and at a bath temperature of 25° C. A rotary evaporator is preferably used.

The amount of active molecule with respect to the phospholipid can be, for example, of approximately 15%, expressed in wt %.

A preferred medicament of the invention consists of a liposome charged with at least one compound of formula (I).

Preferably, the compound(s) of formula (I) constitute the only active ingredient(s) contained in the pharmaceutical composition according to the invention, in particular when said pharmaceutical composition is a liposome. Said liposome comprising at least one compound of formula (I) can be administered, for example, by oral route or by parenteral route.

Alternatively, the compound of formula (I) can be used in combination with another active ingredient, such as for example an anticancer agent, in particular avastin, irinotecan, temozolomide or taxol derivatives.

The pharmaceutical compositions according to the invention can be in any suitable form for oral administration or for parenteral administration, in particular by injection, infusion or inhalation, known to a person skilled in the art.

In particular, said pharmaceutical composition can be a pharmaceutically acceptable solution, in particular an alcoholic solution, of at least one compound of formula (I), alone or in combination with another active ingredient, which can be administered to a patient by transfusion or infusion.

Said pharmaceutical composition can, in particular, be suitable for administration by oral or sublingual route. Besides the usual pharmaceutical forms, for example tablets, capsules, powders, granules, solutions, emulsions, oral suspensions, drops, syrups, etc., the oral pharmaceutical compositions according to the invention can comprise complexes of compounds of formula (I) with biliary salts, or, for example, combinations of compounds of formula (I) with phospholipids, such as phosphatidylcholine, in liposomal or non-liposomal form.

The compounds of formula (I), for use in the treatment of diseases involving transformed astrocyte cells, in particular in the treatment of glioblastoma multiforme or grade IV astrocytoma (GBM), are also a subject of the invention. In particular, the compounds of formula (I) can be injected directly into the cerebral cortex, at the treatment site.

The invention also relates to the treatment of diseases involving transformed astrocyte cells, in particular the treatment of glioblastoma multiforme or grade IV astrocytoma (GBM), by administering an effective amount of at least one compound of formula (I).

The invention also relates to the treatment of other cancers, namely malignant haemopathies of the myeloid type and lymphomas, neuroblastomas and melanomas.

The compounds of formula (I), for use in the treatment of malignant haemopathies of the myeloid type, are also a subject of the invention.

The invention also relates to the treatment of malignant haemopathies of the myeloid type, by administering an effective amount of at least one compound of formula (I).

Malignant pathologies of the myeloid type develop from a normal myeloid cell. Now, this cell type, in the normal state, has an energy metabolism fairly similar to that of the astrocyte: it produces its energy from mitochondrial respiration and from glycolysis (lactate pathway; LDH) (13). In the case of cancers of myeloid origin, the cancer cells produce their energy from glycolysis. As for GBM, the anti-cancer activity of the compounds of formula (I) would be due to inhibition of LDH (glycolysis) and, consequently, overheating of the cell caused by a high burst of mitochondrial respiration.

The compounds of formula (I), for use in the treatment of lymphomas, are also a subject of the invention.

The invention also relates to the treatment of lymphomas, by administering an effective amount of at least one compound of formula (I).

In fact, as the myeloid line and the lymphoid line have a common origin, which is the pluripotent haematopoietic stem cell, the activity of the compounds of formula (I) on malignant haemopathies of the myeloid type means their use can also be envisaged for treating lymphomas.

The compounds of formula (I), for use thereof in the treatment of neuroblastomas, are also a subject of the invention.

The invention also relates to the treatment of neuroblastomas, by administering an effective amount of at least one compound of formula (I).

Regarding neuroblastomas, which mainly affect the extracranial sympathetic nervous system, the compounds of formula (I) display an anti-tumour activity because, as with the astrocyte, the neuron has the same embryological origin, on the one hand, namely the ectoderm, and cellular origin, on the other hand, namely the neuroepithelial cells (14). In short, the astrocyte and the neuron are both nerve cells and are equally susceptible to the compounds of formula (I).

The compounds of formula (I), for use in the treatment of melanomas, are also a subject of the invention.

The invention also relates to the treatment of melanomas, by administering an effective amount of at least one compound of formula (I).

In fact, the melanocytes, which are at the origin of melanomas, are derived from the neural crest, itself derived from the ectoderm (14). Since the astrocytes and the neurons are also derived from the ectoderm, and the compounds of formula (I) display anti-GBM and anti-neuroblastoma activity, these compounds are also likely to have anti-cancer properties with respect to melanomas.

According to an alternative, said treatment is a sequential treatment that comprises at least one step of administering a first compound of formula (I) and at least one step of administering a second compound of formula (I), different from the first.

The following examples illustrate the invention but do not limit it.

Section I concerns chemical synthesis.

Examples 1 and 2 concern the preparation of synthesis intermediates used for preparing the compounds of formula (I). Examples 3 to 6 concern the preparation of compounds of formula (I).

Section II concerns the biological activity of the compounds of formula (I).

I/ Chemical Synthesis

EXAMPLE 1

Preparation of 7beta-acetylcholesterol (compound 1.4)

The reaction diagram is shown in FIG. 1.
1) Preparation of Compound 1.1

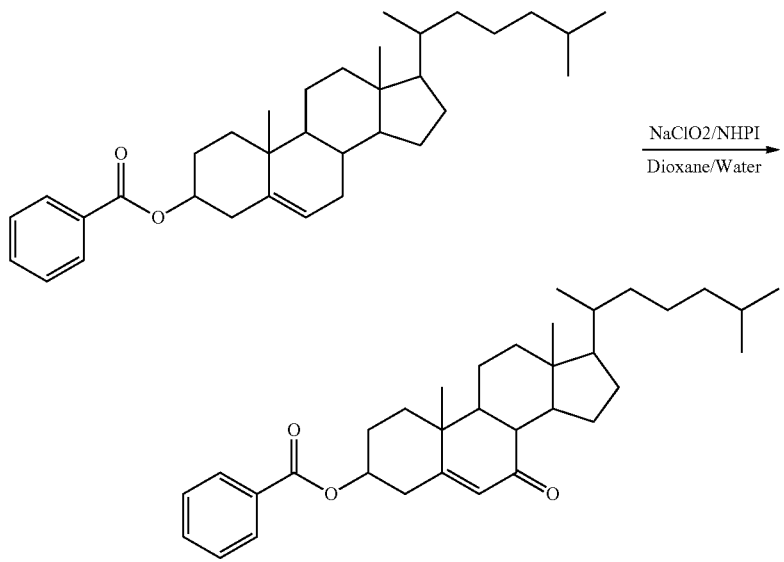

The following reagents were used:

|  | MW | Nb mol. | eq | Mass or Volume |
|---|---|---|---|---|
| Cholesteryl benzoate | 490.78 | 100 mmol | — | 50 g |
| Sodium Chlorite | 90.44 | 300 mmol | 3 eq | 28 g |
| N-Hydroxyphthalimide | 163.13 | 10 mmol | 0.1 eq | 1.7 g |
| Dioxane/Water 3/1 |  |  |  | 500 ml |

The cholesteryl benzoate, dioxane/water mixture, sodium chlorite and N-hydroxyphthalimide are placed in that order in a 1-litre three-necked flask equipped with a condenser. This mixture is heated at 50° C. for 6 h. The progress of the reaction is monitored by silica plate TLC (TLC silica gel 60 F254, Merck) in hexane/Et2O 8/2.

When the rate of formation reaches an acceptable value, the crude reaction mixture is poured into a 10% solution of sodium sulphite (500 ml), and then extracted with ether. The organic phase obtained is washed with a saturated solution of sodium hydrogen carbonate, then with water and finally with brine. This organic phase is then dried over sodium sulphate, filtered and then evaporated under reduced pressure.

The coloured oily residue obtained is then purified by recrystallization from ethanol. As the white solid obtained is not of sufficient purity, it is purified again by silica gel chromatography (silica SDS 60A, 35-70 μm). A solid deposit is obtained by taking up this oil in dichloromethane. Purification is carried out in an eluent ranging from 98/2 hexane/ethyl acetate to 90/10. The product is obtained in the form of a white solid.

Yield: 23%

Analyses: Analysis by $^1$H NMR in CDCl$_3$, BRUKER 400 MHz. HPLC column normal phase CHIRALCEL O-DH (ODH0CE-CE026 column), eluent 9/1 Hexane/iProH, 20 min, wavelength 190 nm.

Retention time 6.682 min, HPLC purity 99.2%.

$^1$H NMR (CDCl$_3$, 400.13 MHz): δ 0.71 (s, 3H, CH$_3$), 0.89 (dd, 6H, 2CH$_3$), 0.94 (d, 3H, CH$_3$), 1.02-2.78 (m, 26H), 1.27 (s, 3H, CH$_3$), 4.99 (m, 1H, CH), 5.76 (d, 1H, CH), 7.44-8.05 (m, 5H, CHAr).

2) Preparation of Compound 1.2

| | MW | Nb mol. | eq | Mass or Volume |
|---|---|---|---|---|
| CeCl$_3$•7H2O | 372.60 | 14.2 mmol | 0.9 eq | 5.3 g |
| THF/MeOH 1:1 | | | | 200 ml |

The ketocholesteryl benzoate, the THF/MeOH solvent mixture and the hydrated cerium chloride are placed in a 500-ml flask. The crude reaction mixture is then cooled to 0° C. with an ice bath, before slowly adding sodium borohydride. Emission of gas is observed, the ice bath is maintained for 1 h, then it is stirred at ambient temperature for 18 h. The progress is monitored by TLC (TLC silica gel 60 F254, Merck) in 80/20 Hexane/EtOAc eluent. If the rate of formation is insufficient, 0.5 eq of sodium borohydride is added.

50 ml of water and 200 ml of dichloromethane are added to the crude reaction mixture. After transfer to a separating funnel, the organic phase is recovered. The aqueous phase is extracted with DCM again. The organic phases are combined, washed with a 1N hydrochloric acid solution and then with a saturated solution of NaCl.

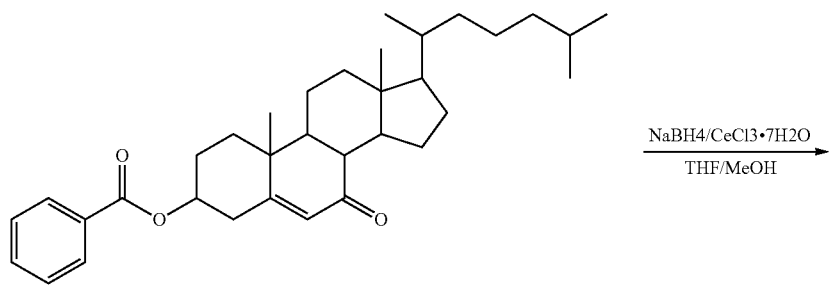

The following reagents were used:

| | MW | Nb mol. | eq | Mass or Volume |
|---|---|---|---|---|
| Ketocholesteryl benzoate | 504.76 | 15.8 mmol | — | 8 g |
| NaBH$_4$ | 37.83 | 7.9 mmol | 0.5 eq + 0.5 eq | 0.3 g + 0.3 g |

The organic phase is then dried over sodium sulphate, filtered and evaporated under reduced pressure, giving a slightly coloured oil, which crystallizes spontaneously.

A solid deposit is obtained by taking up the residue in DCM. This crude product is purified on a silica gel column (silica SDS 60A, 35-70 μm) in 9/1 hexane/EtOAc eluent. The product is obtained in the form of a white solid.

Yield: 89%

Analysis: Analysis by $^1$H NMR in CDCl$_3$, BRUKER 400 MHz. HPLC column normal phase CHIRALCEL O-DH (ODH0CE-CE026 column), eluent 9/1 hexane/iProH, 20 min, wavelength 190 nm.

Retention time 7.076 min, HPLC purity 98.8%.

$^1$H NMR (CDCl$_3$, 400.13 MHz): δ 0.63 (s, 3H, CH$_3$), 0.79 (dd, 6H, 2CH$_3$), 0.85 (d, 3H, CH$_3$), 0.89-2.43 (m, 27H), 1.04 (s, 3H, CH$_3$), 3.81 (d, 1H, CH), 4.81 (m, 1H, CH), 5.29 (d, 1H, CH), 7.34-7.99 (m, 5H, CHAr).

3) Preparation of Compound 1.3

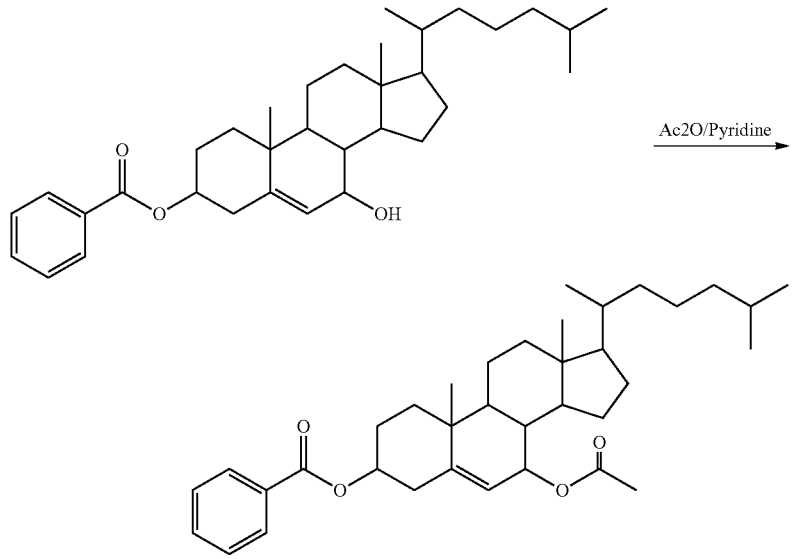

The following reagents were used:

|  | MW | Nb mol. | eq | Mass or Volume |
|---|---|---|---|---|
| 7-β-Hydroxycholesteryl benzoate | 505.76 | 9.9 mmol | — | 5 g |
| Acetic anhydride |  |  |  | 20 ml |
| Pyridine |  |  |  | 20 ml |

The 7-β-hydroxycholesteryl benzoate, pyridine, and then the acetic anhydride are placed in a 100-ml flask. This mixture is stirred at ambient temperature for 16 h. The progress is monitored by TLC (TLC silica gel 60 F254, Merck) in 9/1 hexane/EtOAc eluent.

The crude reaction mixture is evaporated under reduced pressure. Two coevaporations with ethyl acetate are carried out. The residue obtained is taken up in ethyl acetate. The organic phase thus obtained is washed with 1N hydrochloric acid, dried over sodium sulphate and then evaporated under reduced pressure.

The white solid obtained is used in the next step directly, without additional purification.

Yield: 100%

Analysis: Analysis by $^1$H NMR in CDCl$_3$, BRUKER 400 MHz. HPLC column normal phase CHIRALCEL O-DH (ODH0CE-CE026 column), eluent 9/1 hexane/iProH, 20 min, wavelength 190 nm.

Retention time 4.972 min, HPLC purity 99.6%.

$^1$H NMR (CDCl$_3$, 400.13 MHz): δ 0.63 (s, 3H, CH$_3$), 0.79 (dd, 6H, 2CH$_3$), 0.84 (d, 3H, CH$_3$), 0.91-2.41 (m, 26H), 1.06 (s, 3H, CH$_3$), 1.95 (s, 3H, CH$_3$ acetyl), 4.78 (m, 1H, CH), 4.99 (d, 1H, CH), 5.21 (s, 1H, CH), 7.33-7.98 (m, 5H, CHAr).

4) Preparation of Compound 1.4

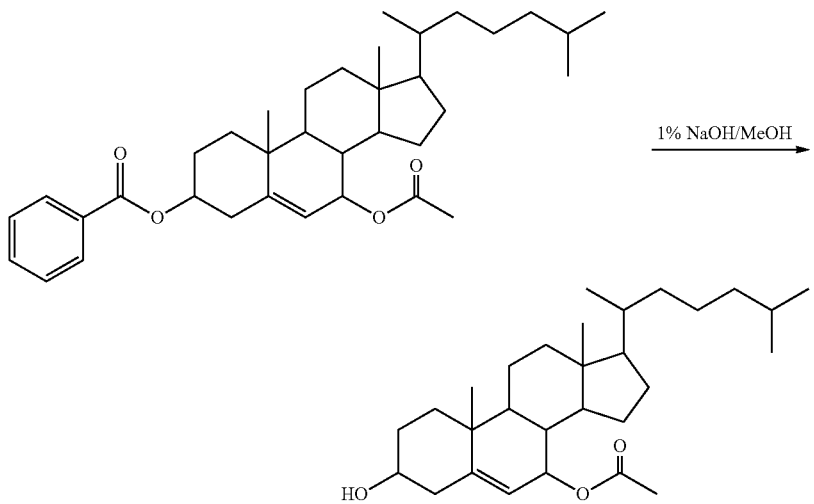

The following reagents were used:

|  | MW | Nb mol. | eq | Mass or Volume |
|---|---|---|---|---|
| 7-β-Acetylcholesteryl benzoate | 548.81 | 9.1 mmol | — | 5 g |
| 1% NaOH in methanol |  |  |  | 50 ml |

The 7-β-acetylcholesteryl benzoate and 1% sodium hydroxide solution in methanol are placed in a 100-ml flask. This mixture is stirred at ambient temperature until completely dissolved. The progress is monitored by TLC (TLC silica gel 60 F254, Merck) in a 7/3 hexane/EtOAc eluent.

In order to complete the reaction, the crude mixture can be heated at 40° C., in that case monitoring by TLC is carried out every 20 minutes.

200 ml of ethyl acetate and 50 ml of water are added, followed by transfer to a separating funnel and separation of the phases. The aqueous phase is extracted with ethyl acetate again. The organic phases are combined, dried over sodium sulphate, filtered and then evaporated under reduced pressure, giving an oily residue.

The residue is taken up in ethyl acetate in order to prepare the solid deposit. Purification is carried out on a silica gel column (silica SDS 60A, 35-70 μm) in hexane/EtOAc eluent ranging from 9/1 to 7/3. The expected product is obtained in the form of a colourless oil which crystallizes spontaneously, giving a white solid. The column is washed with 100% ethyl acetate in order to recover the 7-β-hydroxycholesterol formed.

Yield: 38%

Analysis: Analysis by $^1$H NMR in CDCl$_3$, BRUKER 400 MHz. HPLC column normal phase CHIRALCEL O-DH (ODH0CE-CE026 column), eluent 9/1 hexane/iProH, 20 min, wavelength 190 nm.

Retention time 6.186 min, HPLC purity 91.7%.

$^1$H NMR (CDCl$_3$, 400.13 MHz): δ 0.62 (s, 3H, CH$_3$), 0.78 (dd, 6H, 2CH$_3$), 0.85 (d, 3H, CH$_3$), 0.86-2.28 (m, 27H), 1.03 (s, 3H, CH$_3$), 1.96 (s, 3H, CH$_3$ acetyl), 3.47 (m, 1H, CH), 4.94 (td, 1H, CH), 5.13 (t, 1H, CH).

EXAMPLE 2

Preparation of
7beta-tert-butyloxycarbonylcholesterol (compound 1.6)

Figure 2:
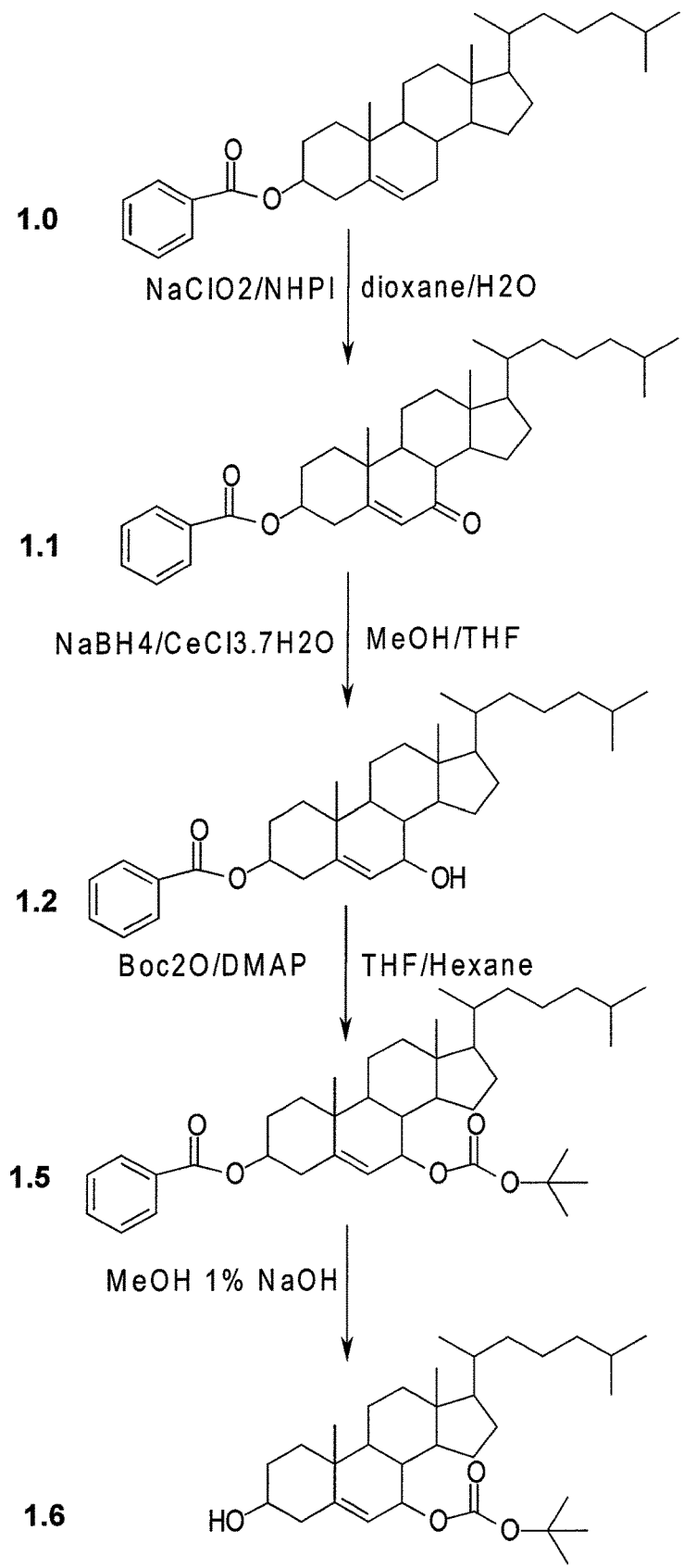
FIG. 2 shows the reaction diagram for the preparation of 7beta-tert-butyloxycarbonylcholesterol (compound 1.6).

The reaction diagram is shown in FIG. 2.
Compound 1.6 is prepared from compound 1.2 from Example 1.
1) Preparation of Compound 1.5

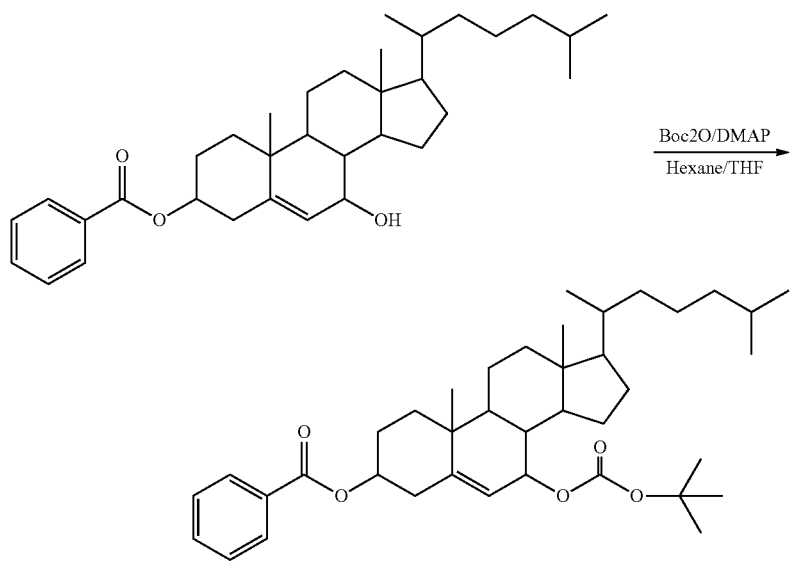

The following reagents were used:

|  | MW | Nb mol. | eq | Mass or Volume |
|---|---|---|---|---|
| 7-β-Hydroxycholesteryl benzoate | 505.76 | 1.29 mmol | — | 0.65 g |
| Boc2O | 218.25 | 2.8 mmol | 2.2 eq | 0.61 g |
| DMAP | 122.17 | 0.13 mmol | 0.1 eq | 0.016 g |
| Hexane/THF 5:2 |  |  |  | 42 ml |

The 7-β-hydroxycholesteryl benzoate, solvent, 2,6-dimethylaminopyridine and then the tert-butyloxycarbonyl anhydride are placed in a 100 ml single-necked flask. This mixture is stirred at ambient temperature until completely dissolved. The progress is monitored by TLC in 8/2 hexane/EtOAc eluent.

50 ml of EtOAc and 10 ml of water are added. The organic phase thus obtained is dried over sodium sulphate, filtered and then evaporated under reduced pressure, giving an oily residue.

The residue is taken up in EtOAc in order to prepare the solid deposit. Purification is carried out on a silica gel column in 95/5 hexane/EtOAc eluent.

Analysis: Analysis by $^1$H NMR in $CDCl_3$.

$^1$H NMR ($CDCl_3$, 400.13 MHz): δ 0.59 (s, 3H, $CH_3$), 0.77 (dd, 6H, $2CH_3$), 0.84 (d, 3H, $CH_3$), 0.86-1.98 (m, 24H), 1.09 (s, 3H, $CH_3$), 1.41 (s, 9H, $3CH_3$, t-Boc), 2.42 (m, 2H, $CH_2$), 4.80 (m, 1H, CH), 4.91 (d, 1H, CH), 5.18 (s, 1H, CH), 7.34-7.97 (m, 5H, CHAr).

2) Preparation of Compound 1.6

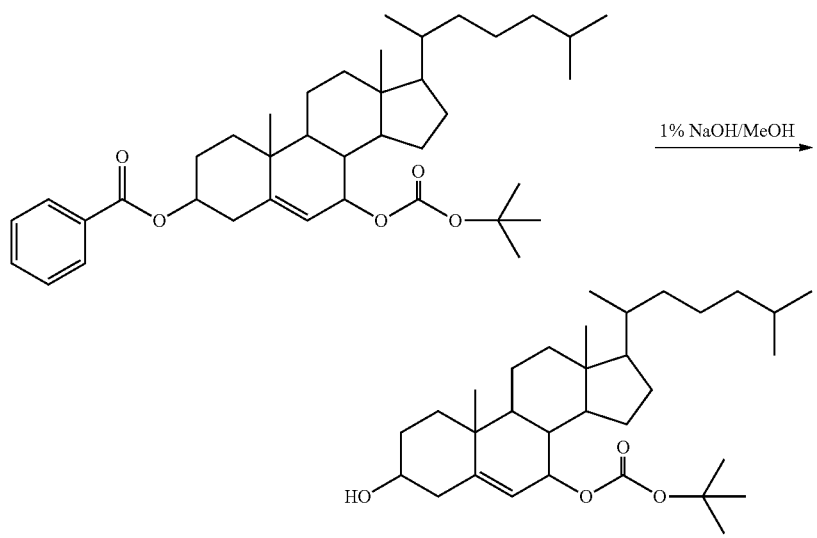

The following reagents were used:

|  | MW | Nb mol. | eq | Mass or Volume |
|---|---|---|---|---|
| 7-β-t-Butyloxycarbonyl-cholesteryl benzoate | 606.89 | 1.64 mmol | — | 1 g |
| 1% NaOH MeOH |  |  |  | 50 ml |

The 7-β-t-butyloxycarbonylcholesteryl benzoate and 1% sodium hydroxide solution in methanol are placed in a 50 ml single-necked flask. This mixture is stirred at ambient temperature until completely solubilized. The progress is monitored by TLC in a 7/3 hexane/EtOAc eluent. In order to complete the reaction, the crude mixture can be heated to 40° C.

100 ml of EtOAc and 20 ml of water are added. The aqueous phase is extracted again with EtOAc. The organic phases are combined, dried over sodium sulphate, filtered and then evaporated under reduced pressure, giving an oily residue.

The residue is taken up in EtOAc in order to prepare the solid deposit. Purification is carried out on a silica gel column in hexane/EtOAc eluent ranging from 9/1 to 7/3. The column is washed with 100% EtOAc in order to recover the 7-β-hydroxycholesterol formed.

Analysis: Analysis by $^1$H NMR in CDCl$_3$.
$^1$H NMR (CDCl$_3$, 400.13 MHz): δ 0.60 (s, 3H, CH$_3$), 0.78 (dd, 6H, 2CH$_3$), 0.84 (d, 3H, CH$_3$), 0.91-2.29 (m, 27H), 0.97 (s, 3H, CH$_3$), 1.41 (s, 9H, 3CH$_3$, t-Boc), 3.47 (m, 1H, CH$_B$), 4.77 (td, 1H, CH$_C$), 5.17 (t, 1H, CH$_A$).

EXAMPLE 3

Preparation of 7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)acetamido)propanoate (molecule 1.a)

Simplified name: 3-benzyloxycarbonyl-glycinyl-alanyl-7-β-O-tert-butyloxycarbonyl-cholesterol

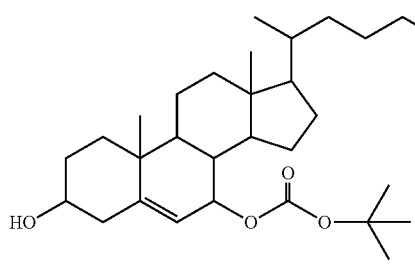

Molecule 1.a is prepared from intermediate compound 1.6.

The following reagents were used:

|  | MW | Nb mol. | eq | Mass or Volume |
|---|---|---|---|---|
| 7-β-t-Butyloxycarbonyl-cholesterol (compound 1.6) | 502 | 0.16 mmol | — | 80 mg |
| Z-Gly-Ala-COOH | 280.28 | 0.24 mmol | 1.5 eq | 68 mg |
| DCC | 206.3 | 0.24 mmol | 1.5 eq | 50 mg |
| DMAP | 122.17 | 0.24 mmol | 1.5 eq | 30 mg |
| THF/DCE 1:1 |  |  |  | 6 ml |

80 mg (0.16 mmol) of 7-β-t-butyloxycarbonylcholesterol, 68 mg (0.24 mmol, 1.5 eq) of dipeptide, 6 ml of solvent mixture (THF/DCE 1:1), 50 mg (0.24 mmol, 1.5 eq) of DCC, and 30 mg (0.24 mmol, 1.5 eq) of DMAP are placed in a 10-ml Wheaton bottle. The crude reaction mixture is stirred for 24 h at ambient temperature. The progress is monitored by TLC in a 7/3 hexane/ethyl acetate eluent.

30 ml of ethyl acetate and 10 ml of water are added to the crude reaction product. The organic phase is separated, dried over sodium sulphate, filtered and then evaporated under reduced pressure. The oily residue obtained is taken up in ethyl acetate in order to prepare the solid deposit.

Purification is carried out on a silica gel column in 7/3, then 6/4, hexane/ethyl acetate eluent.

Analysis: Analysis by $^1$H NMR in CDCl$_3$.

$^1$H NMR (CDCl$_3$, 400.13 MHz): δ 0.60 (s, 3H, CH$_3$), 0.79 (dd, 6H, 2CH$_3$), 0.83 (d, 3H, CH$_3$), 0.94-1.88 (m, 24H), 0.98 (s, 3H, CH$_3$), 1.19 (s, 3H, CH$_3$ Ala), 1.40 (s, 9H, 3CH$_3$, t-Boc), 2.27 (m, 2H, CH$_2$), 3.83 (m, 2H, CH$_2$), 4.47 (td, 1H, CH Ala), 4.47 (m, 1H, CH), 4.78 (td, 1H, CH), 5.07 (s, 2H, CH$_2$ Gly), 5.22 (t, 1H, CH), 5.23 (m, 1H, NH), 6.41 (sl, 1H, NH), 7.29 (m, 5H, CHAr).

EXAMPLE 4

Preparation of 7-acetoxy-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)acetamido)propanoate (molecule 1.b)

Simplified name: 3-benzyloxycarbonyl-glycinyl-alanyl-7-β-O-acetylcholesterol

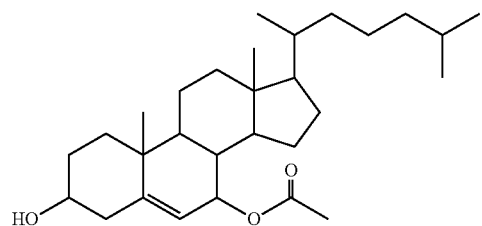

-continued

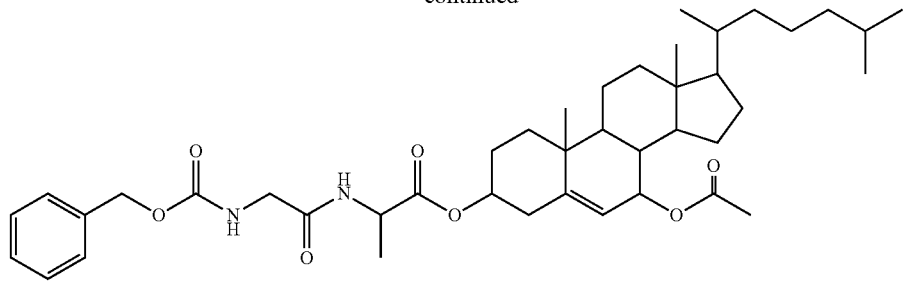

Molecule 1.b is prepared from intermediate compound 1.4.

The following reagents were used:

|  | MW | Nb mol. | eq | Mass or Volume |
|---|---|---|---|---|
| 7-β-Acetylcholesterol | 444 | 0.18 mmol | — | 80 mg |
| Z-Gly-Ala-COOH | 280.28 | 0.27 mmol | 1.5 eq | 76 mg |
| DCC | 206.3 | 0.27 mmol | 1.5 eq | 56 mg |
| DMAP | 122.17 | 0.27 mmol | 1.5 eq | 33 mg |
| THF/DCE 1:1 |  |  |  | 6 ml |

60 mg (0.13 mmol) of 7-β-acetylcholesterol, 70 mg (0.19 mmol, 1.5 eq) of dipeptide, 6 ml of solvent mixture (THF/DCE 1:1), 42 mg (0.19 mmol, 1.5 eq) of DCC, and 25 mg (0.19 mmol, 1.5 eq) of DMAP are placed in a 10-ml Wheaton bottle. The crude reaction mixture is stirred for 24 h at ambient temperature.

The progress is monitored by TLC in 7/3 hexane/ethyl acetate eluent.

30 ml of ethyl acetate and 10 ml of water are added to the crude reaction product. The organic phase is separated, dried over sodium sulphate, filtered and then evaporated under reduced pressure. The oily residue obtained is taken up in ethyl acetate in order to prepare the solid deposit.

Purification is carried out on a silica gel column in 7/3, then 6/4 hexane/ethyl acetate eluent.

Analysis: Analysis by $^1$H NMR in CDCl$_3$.

$^1$H NMR (CDCl$_3$, 400.13 MHz): δ 0.62 (s, 3H, CH$_3$), 0.78 (dd, 6H, 2CH$_3$), 0.84 (d, 3H, CH$_3$), 0.91-1.83 (m, 25H), 1.01 (s, 3H, CH$_3$), 1.17 (s, 3H, CH$_3$ Ala), 1.94 (s, 3H, CH$_3$ acetyl), 2.27 (m, 2H, CH$_2$), 3.82 (m, 1H, CH), 4.47 (td, 1H, CH Ala), 4.56 (m, 1H, CH), 4.95 (td, 1H, CH), 5.06 (s, 2H, CH$_2$ Gly), 5.17 (sl, 1H, CH), 5.37 (t, 1H, CH), 6.49 (dl, 1H, NH), 7.24 (m, 5H, CHAr).

EXAMPLE 5

Preparation of 7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl-1,3-dioxolane-4-carboxylate (molecule 2.a)

Simplified name: 3-(S)-2,2-dimethyl-1,3-dioxolane-4-carboxyl-7-β-O-tert-butyloxycarbonyl-cholesterol 1) Preparation of the Dimethyl-1,3-Dioxolane-4-Carboxylate Group

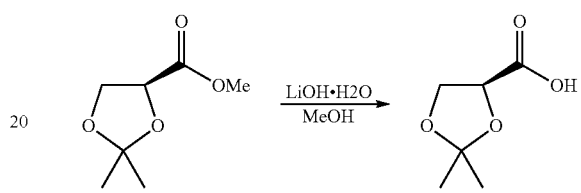

The following reagents were used:

|  | MW | Nb mol. | eq | Mass or Volume |
|---|---|---|---|---|
| (—)-Methyl (S)-2,2-dimethyl-1,3-dioxolane-4-carboxylate | 160.17 | 31.2 mmol | — | 5 g |
| LiOH•H$_2$O | 41.96 | 78 mmol | 2.5 eq | 3.3 g |
| Methanol |  |  |  | 25 ml |

The acetal, methanol and then the lithium hydroxide are placed in a 50-ml flask. This mixture is stirred at ambient temperature for 16 h.

The crude reaction mixture is evaporated under reduced pressure. The residue obtained is taken up in 75 ml of water. This phase is then acidified at 0° C. to pH 1 with 1N hydrochloric acid, then extracted with 2×100 ml of ethyl acetate. The organic phases are combined, dried over sodium sulphate, filtered and then evaporated under reduced pressure, giving a slightly coloured oily residue.

The residue is used directly in the coupling step without additional purification.

Analysis: Analysis by $^1$H NMR in DMSO, BRUKER 400 MHz.

$^1$H NMR (CDCl$_3$, 400.13 MHz): δ 1.32 (d, 3H, CH$_3$), 1.42 (s, 3H, CH$_3$), 4.14 (AB, 2H, CH$_2$), 4.55 (dd, 1H, CH), 10.30 (sl, 1H, OH), 7.24 (m, 5H, CHAr).

Yield: 94%

2) Preparation of Molecule 2.a

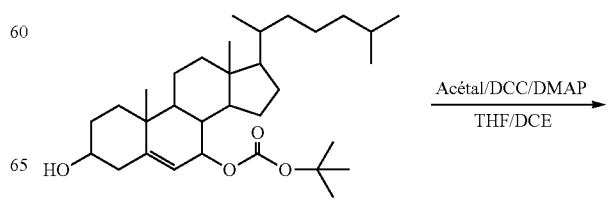

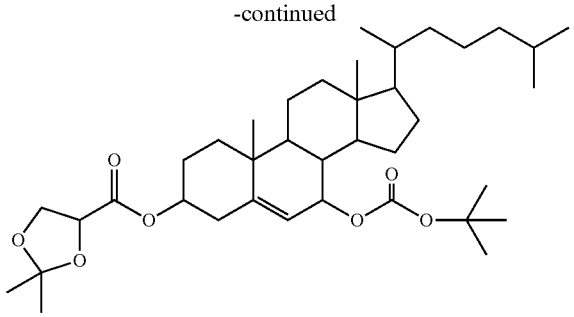

Molecule 2.a is prepared from intermediate compound 1.4.

The following reagents were used:

|  | MW | Nb mol. | eq | Mass or Volume |
|---|---|---|---|---|
| 7-β-Acetylcholesterol | 444 | 3.4 mmol | — | 1.5 g |
| 3-(S)-2,2-Dimethyl-1,3-dioxolane-4-carboxylic acid | 146.17 | 10.1 mmol | 3 eq | 1.35 g |
| DCC | 206.3 | 10.1 mmol | 3 eq | 2.1 g |
| DMAP | 122.17 | 10.1 mmol | 3 eq | 1.24 mg |
| THF/DCE (1:1) |  |  |  | 50 ml |

50 mg (9.9 mmol) of 7-β-t-butyloxycarbonylcholesterol, 6 ml of solvent mixture (THF/DCE 1:1), and 16 mg (11.9 mmol, 1.2 eq) of 3-(S)-2,2-dimethyl-1,3-dioxolane-4-carboxylic acid are placed in a 10-ml Wheaton bottle.

24.5 mg (11.9 mmol, 1.2 eq) of DCC and 14.5 mg (11.9 mmol, 1.2 eq) of DMAP are added, before stirring the crude reaction mixture for 24 h at ambient temperature. The progress is monitored by TLC in 8/2 hexane/ethyl acetate eluent. It is heated at 50° C. for 2 h in order to end the reaction.

30 ml of ethyl acetate and 10 ml of water are added to the crude reaction product. The organic phase is separated, dried over sodium sulphate, filtered and then evaporated under reduced pressure. The oily residue obtained is taken up in ethyl acetate in order to prepare the solid deposit.

Purification is carried out on a silica gel column in 95/5, then 9/1 hexane/ethyl acetate eluent.

Analysis: Analysis by $^1$H NMR in CDCl$_3$.

$^1$H NMR (CDCl$_3$, 400.13 MHz): δ 0.60 (s, 3H, CH$_3$), 0.79 (dd, 6H, 2CH$_3$), 0.83 (d, 3H, CH$_3$), 0.74-1.97 (m, 25H), 0.98 (s, 3H, CH$_3$), 1.33 (s, 3H, CH$_3$ Acetal), 1.40 (s, 9H, 3CH$_3$, t-Boc), 1.42 (s, 3H, CH$_3$ Acetal), 2.29 (m, 2H, CH$_2$), 4.08 (AB, 2H, CH$_2$ Acetal), 4.48 (ddd, 1H, CH Acetal), 4.63 (m, 1H, CH), 4.78 (td, 1H, CH), 5.22 (d, 1H, CH).

EXAMPLE 6

Preparation of 7-acetoxy-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl-1,3-dioxolane-4-carboxylate (molecule 2.b)

Simplified name: 3-(S)-2,2-dimethyl-1,3-dioxolane-4-carboxyl-7-β-O-acetylcholesterol

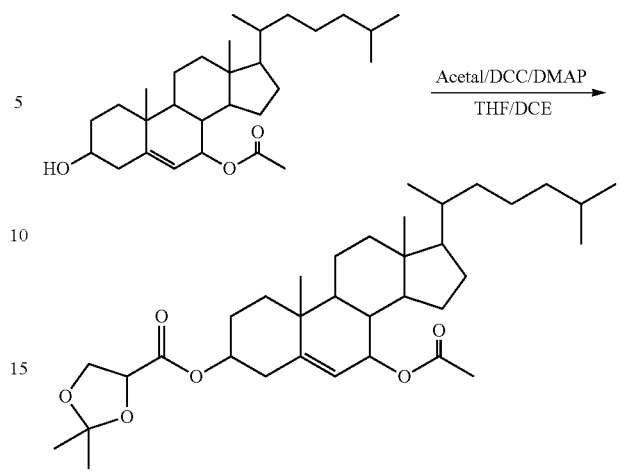

Molecule 2.b is prepared from intermediate compound 1.4.

The following reagents were used:

|  | MW | Nb mol. | eq | Mass or Volume |
|---|---|---|---|---|
| 7-β-Acetylcholesterol | 444 | 3.4 mmol | — | 1.5 g |
| 3-(S)-2,2-Dimethyl-1,3-dioxolane-4-carboxylic acid | 146.17 | 10.1 mmol | 3 eq | 1.35 g |
| DCC | 206.3 | 10.1 mmol | 3 eq | 2.1 g |
| DMAP | 122.17 | 10.1 mmol | 3 eq | 1.24 mg |
| THF/DCE (1:1) |  |  |  | 50 ml |

The cholesterol, the solvent mixture and the acid are placed in a 100-ml flask. DCC and DMAP are added, before stirring the crude reaction product for 24 h at ambient temperature. The progress is monitored by TLC (TLC silica gel 60 F254, Merck) in 8/2 hexane/EtOAc eluent.

100 ml of ethyl acetate and 50 ml of water are added to the crude reaction mixture. The organic phase is separated, dried over sodium sulphate, filtered and then evaporated under reduced pressure.

The oily residue obtained is taken up in ethyl acetate in order to prepare the solid deposit. Silica gel column (silica SDS 60A, 35-70 µm) in 95/5, then 9/1 hexane/EtOAc eluent.

Yield: 68%

Analysis: Analysis by $^1$H and $^{13}$C NMR in CDCl$_3$ BRUKER 400 MHz. HPLC column normal phase CHIRALCEL O-DH (ODH0CE-CE026 column), eluent 9/1 hexane/iProH, 20 min, wavelength 190 nm.

Retention time 5.291 min, HPLC purity 98.7%.

$^1$H NMR (CDCl$_3$, 400.13 MHz): δ 0.62 (s, 3H, CH$_3$), 0.79 (dd, 6H, 2CH$_3$), 0.84 (d, 3H, CH$_3$), 0.91-2.30 (m, 27H), 1.01 (s, 3H, CH$_3$), 1.33 (s, 3H, CH$_3$ Acetal), 1.42 (s, 3H, CH$_3$ Acetal), 1.93 (s, 3H, CH$_3$ acetyl), 4.09 (AB, 2H, CH$_2$ Acetal), 4.48 (dd, 1H, CH Acetal), 4.62 (m, 1H, CH), 4.96 (td, 1H, CH), 5.18 (d, 1H, CH).

II/ Biological Activity

A/ Protocols

The following protocols were used for all the experiments:

1) Cell Cultures

Plastic flat-bottomed 96-well culture plates (NUNC, USA) treated for cell culture (Sigma-Aldrich, ref. 114754)

are used; 1500 cells are seeded per well in 200 µl of culture medium. At the time of treatment, 100 µl of pure culture medium, 100 µl of culture medium containing ethanol, or liposomes, or 100 µl of culture medium containing the active ingredients are added per well; the final volume of the culture medium, after treatment, is therefore 300 µl for all the wells.

The cultures are incubated in a Sanyo incubator (Japan, model MCO-19AlC-UV) at 37° C. and in an atmosphere with 5% $CO_2$ and saturated in humidity. The cells are observed with an inverted microscope (Nikon Eclipse TS100, Japan) and the photographs are taken with a camera (DIGITAL camera with c-mount; LABOVER, France). The culture hood is a microbiological safety hood MSC (thermo SCIENTIFIC, model HERA SAFE KS12, France).

The cell doubling time is calculated using the formula:

$$\text{Doubling time} = (tb-ta)\log(2)/(\log(b)-\log(a))$$

where (a) and (b) represent the number of cells at times ta and tb (tb>ta) (15).

Transition is carried out by dissociation with trypsin (bovine pancreas Type 3, Sigma, France). Cell dissociation is carried out at ambient temperature, for 30 minutes, with a 0.04% (w/v) Tyrode KCl solution containing 0.05% (w/v) trypsin.

After dissociation, the cells are suspended in the culture medium appropriate for the cells and counted using a THOMA cell and diluted in the same medium in order to obtain 1500 cells per well.

a) Cell Lines

The following glioblastoma cells were used:

C6 lines.

The type C6 cell line was obtained by Benda et al. (16) from rat brain tumours, induced by N-methylnitrosourea. This cell type is used as "in vitro" and "in vivo" model for evaluating anti-GBM potential. The lines originate from the former Strasbourg Neurochemistry Centre (U44 INSERM and UPR 416 CNRS).

The culture medium is made up of 70% Minimum Essential Medium (MEM; (Fischer Scientifique, ref. 61100) and 30% Hanks solution (SIGMA, ref. H 9269). The following are added to the culture medium: foetal calf serum (FCS; Fischer Scientifique, ref. 10108165) at a final concentration of 5% (v/v), an antibiotic solution of ciprofloxacin hydrochloride 5 µg/mL (EUROMEDEX, ref. UC5074) and a solution of Fungizone 2.5 µg/mL (INVITROGEN, ref. 15290-026). The doubling time of this cell type is 17 h.

GBM lines of human origin

The human glioblastoma lines (GBM, line U-87 MG) and their culture medium (Eagle's Minimum Essential Medium or EMEM) were obtained from ATCC (USA, ref. ATCC-HTB-14). Culture of the cells is started and maintained according to the recommendations of the ATCC. These lines are commonly used "in vitro" and "in vivo" for testing anti-GBM potential. The doubling time of these lines is 16 h.

The following primary cultures of human cells were also used:

Astrocyte cells

The astrocyte cells of human origin used were obtained from ScienCell, USA (ref. 1800) as well as their culture medium, made up of basic medium containing 2% (v/v) FCS serum (ref. 0010), astrocyte growth proteins (AGS, ref. 1852) and a solution of penicillin/streptomycin (ref. 0503). The doubling time of these human astrocytes is 96 h.

Hepatic cells

Of human origin, they were obtained from ScienCell, USA (ref. 50200) as was the culture medium (ref. 5201), which contains 10% (v/v) FCS. The doubling time of these cells is 24 h.

Renal cells

These cells, of human origin, were obtained from ScienCell, USA (ref. 4120) as was the culture medium (ref. 4101), which contains 10% (v/v) FCS. The doubling time is 96 h.

Cardiac cells

These cells, of human origin, were obtained from ScienCell, USA (ref. 6300) as was the culture medium, which contains 10% (v/v) FCS. The doubling time is 72 h.

Skeletal muscle cells

Of human origin, they were obtained from ScienCell, USA (ref. 3500) as was the culture medium (ref. 3501), which contains 10% (v/v) FCS. The doubling time for these cells is 72 h.

The following cultures of cancer cells of human origin were also used:

Liver cancer cells

They were obtained from ATCC (ref. ATCC-HB-8065). The culture medium consists of MEM (Gibco, USA; ref. 51200) and 10% (v/v) FCS. The doubling time is 60 h.

Prostate cancer cells

They were obtained from ATCC (ref. ATCC-HTB-81). The culture medium is the same as that used for the liver cancer lines. The doubling time is 60 h.

Breast cancer cells

They were obtained from ATCC (ref. ATCC-HTB-19). The culture medium is the same as that used for the liver cancer lines. The doubling time is 20 h.

Colon carcinoma (line HT29/219)

They were obtained from the ECACC collection (Ref. ECACC-85061109). The culture conditions are based on the recommendations in the Sigma-Aldrich information leaflet.

Neuroblastoma (line SH-SY5Y)

They were obtained from the ATCC collection (Ref. ATCC-CRL-2266). The culture conditions are based on the recommendations in the ATCC information leaflet.

Chronic Myelomonocytic Leukaemia (CMML)

The cells purified from blood samples of patients suffering from Chronic Myelomonocytic Leukaemia (CMML) were obtained by the Clinical Haematology Centre and the Biotherapy Centre of the Saint Eloi Hospital (CHU de Montpellier). Culture was carried out by the technique of seeding on a feed layer. The cells are seeded on a feed layer that is not affected by the treatments intended for the cells of interest and that does not greatly alter the physiology of the cells of interest. The CMML cells were cultured on cell lines originating from human embryo spinal cord (17).

For all these cultures, culture was started and maintained according to the suppliers' recommendations.

b) Treatment of the Cultures

The active ingredients are either dissolved in absolute ethanol (AnalaR, NORMAPUR, VWR, France) or in the form of a liposomal solution, such as 10 µl of the stock solutions diluted in 990 µl and then added to the culture wells (200 µl of culture medium) giving concentrations of 30.0, 15.0, 7.5 and 3.3 µM (final volume of culture medium per well BI-GBM: 300 µl).

When the active ingredients are in ethanolic solution, the culture medium contains 3.3% ethanol (v/v).

2) Preparation of the Liposomes a) the Basic Methodology is Described by Werthle et al. (10).

Briefly, the compounds to be tested, namely the compounds according to the invention (active ingredients) or 7β-OHCH—C3-ester (a derivative of 7beta-hydroxysterol esterified in position 3 with an oleate group, the synthesis of which is described by Rakotoarivelo et al. (18) and used as control), soya phosphatidylcholine (Sigma) as well as cholesteryl-3-sulphate (Sigma) are taken from their stock solutions prepared from dichloroethane in the case of the active ingredients and the 7β-OHCH—C3-ester, a chloroform:methanol mixture (9:1, v/v) in the case of phosphatidylcholine and chloroform in the case of cholesteryl-3-sulphate. The molar ratios are 1 M/0.1 M/0.25 M for phosphatidylcholine, cholesteryl-3-sulphate and the 7β-OHCH—C3-ester and the active ingredients respectively.

After evaporation, a solution of PBS saline, without $Ca^{2+}$ and $Mg^{2+}$, pH7.2 (BioRad) is added to the dry compound. The volume of buffer and the mass of the products are adjusted so that 20 or 10 μl of liposomes added to 90 μl of culture medium gives the desired final concentrations. The liposomes are formed by the extrusion technique with Liposofast (Sodexim, SA Muizon, France). The solution is passed through polycarbonate filtration membranes (100 nm) 41 times. The liposomes are sterilized by filtration on 22 μm Millipore membranes.

For the tests of activities of the molecules on other human cell types "in vitro", the manufacture of the liposomes was optimized in two different ways, as described above, namely with respect to homogeneous size distribution, on the one hand, and with respect to the concentration of active molecule, on the other hand.

b) Obtaining Liposomes with Identical Size Distribution and with a Composition that is Stable Over Time ("Improved Liposomes").

After evaporation of the solvents, the lipid film is again dissolved in dichloroethane:ethanol (3.3:1.5; v:v) and the solution is evaporated again under a nitrogen stream. One ml of PBS is added while stirring vigorously, the lipid residue is scraped so that it dissolves again, followed by vigorous stirring for 5 min, and then sonication of 10 pulses of 1 min is applied at a temperature not exceeding 20° C. (Elma, S 60H, Elmasonic). The vesicles obtained are extruded and sterilized as described above, except that the solution is only passed through the filtration membranes twice.

These liposomes have a size distribution from 40 to 80 nm and contain 0.086 mg/ml of molecules 2.b.

c) Obtaining Liposomes with a Higher Concentration of Molecules 2.b. ("Concentrated Liposomes").

For the preparation of the lipid film, the concentration of phosphatidylcholine is doubled; the concentration of the other compounds remains identical to that described above for the improved liposomes.

The procedure for producing these liposomes is identical to that described for the improved liposomes, except that (1) sonication is 20 pulses of 1 min and (2) the solvents are evaporated under reduced pressure (about 3 kPa; 30 mbar) using a rotary evaporator (Buchi, models V 850 and R 215).

These liposomes have a size distribution from 40 to 80 nm and contain 0.133 mg/ml of molecule 2.b.

Characterization of the molecules making up the liposomes, investigation of stability and of the composition of the liposomes are carried out after extraction of the lipid compounds according to the method of Folch et al. (19), except that before extraction, 500 μl of the solution of liposomes is incubated with 10 μl of 2% (v:v) Triton X-100 (Sigma) at 40° C. for 18 h.

Analysis of the fatty acids making up the phosphatidylcholine, after methylation according to routine techniques, is carried out by gas chromatography coupled to mass spectrometry (GC/MS).

Characterization of the choline group of phosphatidylcholine is carried out according to the method of Reineckate (20).

Molecule 2.b is quantified by HPLC as described above (preparation of the compounds) or by silica thin-layer chromatography as described in point 5) below.

The size distribution of the liposomes is measured on fluorescent liposomes and morphometric analysis is carried out by the Sert program after obtaining images with the epifluorescence microscope (Axivert, Zeiss).

The fluorescent liposomes are produced with the same quantity of phosphatidylcholine described for the improved or concentrated liposomes except that the phosphatidylcholine used contains 5.0% fluorescent phosphatidylcholine (NBD-PC-oleyl; Avanti; Excitation/Emission=460 nm/534 nm) in the case of the improved liposomes and 2.5% in the case of the concentrated liposomes.

The liposomes are sedimented on glass culture slides coated firstly with poly-D-lysine (Sigma, 1% in water, w:v) and then with laminin (Sigma, 0.6% in water). The liposomes are fixed with glutaraldehyde (Merck) (liposomes:glutaraldehyde:PBS; 15:37.5:97.5, v:v:v) before obtaining the images.

3) Measurement of Activity and Toxicity

The same methods are used for both cases. For the activity, the anti-GBM potential of the test compounds is used, and the toxicity, is tested on normal cells of human origin maintained "in vitro".

The following measurement methods are used:

a) Cell Counting

A method of cell counting on photographs was used.

For example, in the case of the cultures in 96-well plates and as a function of the magnification of the microscope used (objectives×10 or ×20, oculars×10), a photograph taken represents a field of view with a diameter equal to 1/5 of the diameter of a well. Therefore the total number of cells in a well is equal to 5 times the number of cells per photograph. This technique was compared with a standard technique (trypsinization of the cell layer, centrifugation of the cells, suspension of the cells in physiological saline solution and counting with a THOMA cell) in the case of the C6 cells. The results obtained are identical for both methods.

b) Protein Assay

The culture medium is withdrawn from each well and 50 μl of Laemmli buffer (0.1 ml of Tris, 0.8 ml of glycerol, 1.6 mL of 10% SDS, 8 ml q.s.f ultrapure water) is added per well.

In control wells, 10 μl of a solution of bovine serum albumin range (crystallized BSA, Sigma) is added; the range is from 0 to 20 μg per well. The wells are then supplemented with 40 μl of Laemmli buffer. Finally, 200 μl of solution of BCA reagent is added (Pierce, USA; BCA Protein Assay Kit; ThemoScientific, France).

The culture plates are incubated for 30 min at 37° C. The optical density for each well is read and quantified by a plate reader (BioRad, USA, iMark Microplate reader 12222) at 570 nm.

c) Cell Viability (MTT Test)

This test makes it possible to detect the cellular respiration, especially the mitochondrial respiration. The stock solution of tetrazolium salt MTT (3-(4,5-dimethylthiazol-2-yl)-2,5-diphenyl tetrazolium bromide, Sigma-Aldrich, USA, ref. M5655) is prepared with 10 mg of MIT/ml of PBS buffer (phosphate-buffered saline, SIGMA, ref. D 1408). This solution is added directly to the culture medium in each well; the final concentration of MTT is 25 μg/ml. The plate is then incubated at 37° C. for at least 1 h.

After blue formazan grains appeared, produced mainly by mitochondrial electron transport, photographs were taken in order to count the cells with a high density of formazan grains; this technique is used in the case of the U87-MG lines. Then for this line and the other cultures, the media are removed and 100 μl of dimethylsuiphoxide (DMSO, SDS CARLO ERBA, Italy) is added to dissolve the formazan deposits.

The optical density is read and quantified using the plate reader (BioRad, iMark Microplate reader) at 490 nm.

The viability is sometimes also tested by the trypan blue exclusion technique.

4) Immunolabellinq of the Cells and Obtaining Images

The anti-CD133 (poly, Abnova), anti-GFAP (poly, Sigma), anti-NFL (mono, Santa Cruz) and anti-fibroblast (ERTR7, Santa Cruz) primary antibodies are diluted to 1/100 in the case of the first three antibodies and to 1/50 in the case of the last.

For detecting IDH-R132H (marker of low-grade gliomas (21)), and CD31 (marker of endothelial cells (22)), the primary antibodies used were obtained from Cliniscicences (mouse, dilution 1/20) and from Spring Bioscience (rabbit, dilution 1/250), respectively.

The secondary antibodies corresponding to recognition of the primary antibodies are anti-rabbit antibodies coupled to peroxidase (goat, Sigma), anti-mouse coupled to Dylight 488 (sheep, Sigma), anti-mouse coupled to Dylight 488 (sheep, Sigma) and anti-rat coupled to FITC (rabbit, Sigma). The dilutions are 1/4000, 1/1000, 1/4000 and 1/400 respectively.

IDH1-R132H and CD31 are detected using peroxidase-coupled secondary antibodies. They are obtained from Fischer Scientific (anti-mouse, dilution 1/1000) and from Sigma (anti-rabbit, dilution 1/500) respectively.

The cells are permeabilized for 5 min with 0.1% Triton X-100 (Sigma) in PBS (Fisher Scientific). The nonspecific sites are blocked with 2% BSA (Sigma) in PBS. Incubations are carried out for 1 h at ambient temperature, 48 h at 4° C., 24 h at 4° C. and 1 h at ambient temperature for the anti-CD133, anti-GFAP, anti-NFL and anti-Fibroblast antibodies respectively. Incubation with the secondary antibodies is carried out for 1 h at ambient temperature. The CD133 positive cells are detected by the $DAB/H_2O_2$ system (Sigma), and observed with an optical microscope.

Colorimetric detection of the markers IDH1-R132H and CD31 is carried out with the substrate NOVARED Vector (Eurobio). The coloured cells are also detected by optical microscopy. The fluorescence is detected and the images are obtained using an epifluorescence microscope (Axiovert, Zeiss, Germany).

5) Extraction of the Lipids and Identification of the Oxysterols

The cells are washed with 0.9% NaCl, collected mechanically, suspended in Tris-HCl buffer (10 mM; pH 7.4) and homogenized with a Potter (1000 r.p.m. and 13 reciprocations). Homogenization is carried out in ice. Extraction is carried out at 4° C. after adding 19 volumes of chloroform:methanol (2:1, v/v) for 1 volume of cell suspension according to Folch et al. (19). The organic phase and the aqueous phase are separated by adding 0.2 volume of 0.74% KCl (w/v).

After evaporation of the organic phase in a rotary evaporator (Buchi, R-215, Switzerland), the lipid residue is taken up in chloroform. The TLC layers are prewashed with chloroform:methanol (1:1, v/v) and activated at 100° C. for 1 h. The lipids are eluted with the following system: petroleum ether (boiling point: 60-70° C.): ether:acetic acid (80:20:1.3, v/v/v). The standards deposited are cholesterol, 7-keto-cholesterol, 7beta-OHCH, 7beta-OHCH—C3-ester and the molecule 2.b. The lipids and standards are detected with Maccala reagent. The Rf values are 0.21, 0.09, 0.08, 0.27 and 0.23 for cholesterol, 7-keto-cholesterol, 7beta-OHCH, 7beta-OHCH—C3-ester and molecule 2.b respectively. Calibration ranges from 0.5 to 2 μg for each standard are carried out separately. The intensities of the spots of interest are calculated relative to the standards after scanning the developed thin layers of silica.

The solvents used are of AnalAR or HPLC grade.

6) Analysis of the Activity and the Inhibition of LDH (Lactate Dehydrogenase; EC 1.1.1.27)

The measurements of the activity of LDH and of its inhibition by a routine inhibitor, oxamate (23), were validated by the spectrometric method (24) using the purified LDH of *Lactobacillus leichmannii* (LL) (Sigma) as standard.

Next, the LDH activities and their inhibition were detected by the "in gel assay" technique (25). The source of activity used was LDH LL and LDH, partially purified, from human GBM lines U87-MG (LDH GBM). "In gel assay" detection was carried out after isoelectric focusing (IEF) on electrophoresis gels of the LDH LL and LDH GBM samples.

a) Partial Purification of LDH GBM

The cells collected in phosphate buffer (50 mM, Ph 7.2.Pi) undergo several freeze (−20° C.)/thaw cycles and the cellular material is homogenized. After centrifugation at 10,000 g for 45 min at 4° C., the supernatant is collected and aliquots containing 10% glycerol (v:v) are frozen at −80° C. At the desired time, the aliquots, after thawing, are chromatographed on a filtration column (Biogel P-60, BioRad) prepared in Pi. The volume of gel is 9 ml and the inside diameter of the column is 0.4 cm. Elution is carried out at atmospheric pressure. The first fraction of 1.4 ml is removed and the LDH activity is collected in the next 2 ml. The protein components of this fraction (LDH GBM) were characterized by the SDS PAGE technique, followed by silver nitrate staining, or by Western blot. The molecular weights characteristic of LDH are found (31 kDa, for the sub-unit, or 62 kDa for its association in a dimer).

b) IEF

The mini-gels of 7.5 (T %) and of 2.6 (C %) are poured into Pi with the Ampholines (BioRad) making it possible to form a pH gradient in the range from 7 to 5 after pre-focusing in a cold chamber. The containers used are of the mini-protean 3 type (BioRad). The anode buffer has a pH of 2.0 and the cathode buffer has a pH of 10.0. The LDH LL and LDH GBM samples are deposited without denaturation and focusing is carried out for 210 min increasing the voltage from 100V to 300V in the cold chamber.

c) LDH Activity

The LDH activity is detected by the lactate/NAD/MTT/phenazine methosulphate system (formation of a precipitate of the formazan type in the IEF gel); this system is described in reference (25).

Addition of oxamate (18 mM) or of molecule 2.b, in ethanolic form (36 mM) makes it possible to measure the degree of inhibition of the LDH LL and LDH GBM activities.

B/ Anti-GBM Activity "In Vitro"
B.1. The Animal Model
Cultures of C6 cells (rat) were used under the operating conditions mentioned above (section II, A).

EXAMPLE 7

Anti-GBM Activity "In Vitro" on Cultures of C6 Cells (Rat)

The results obtained are summarized in Table 1 below as well as in FIG. 3.

TABLE 1

| | Molecules tested (ethanol 3%) | | |
|---|---|---|---|
| | 1.a (Ex. 3) 15 µm | 2.a (Ex. 5) 15 µm | 1.a then 2.a 15 µm + 7.5 µm |
| Live residual cells | 3% | 100% | 0% |

Figure 3:
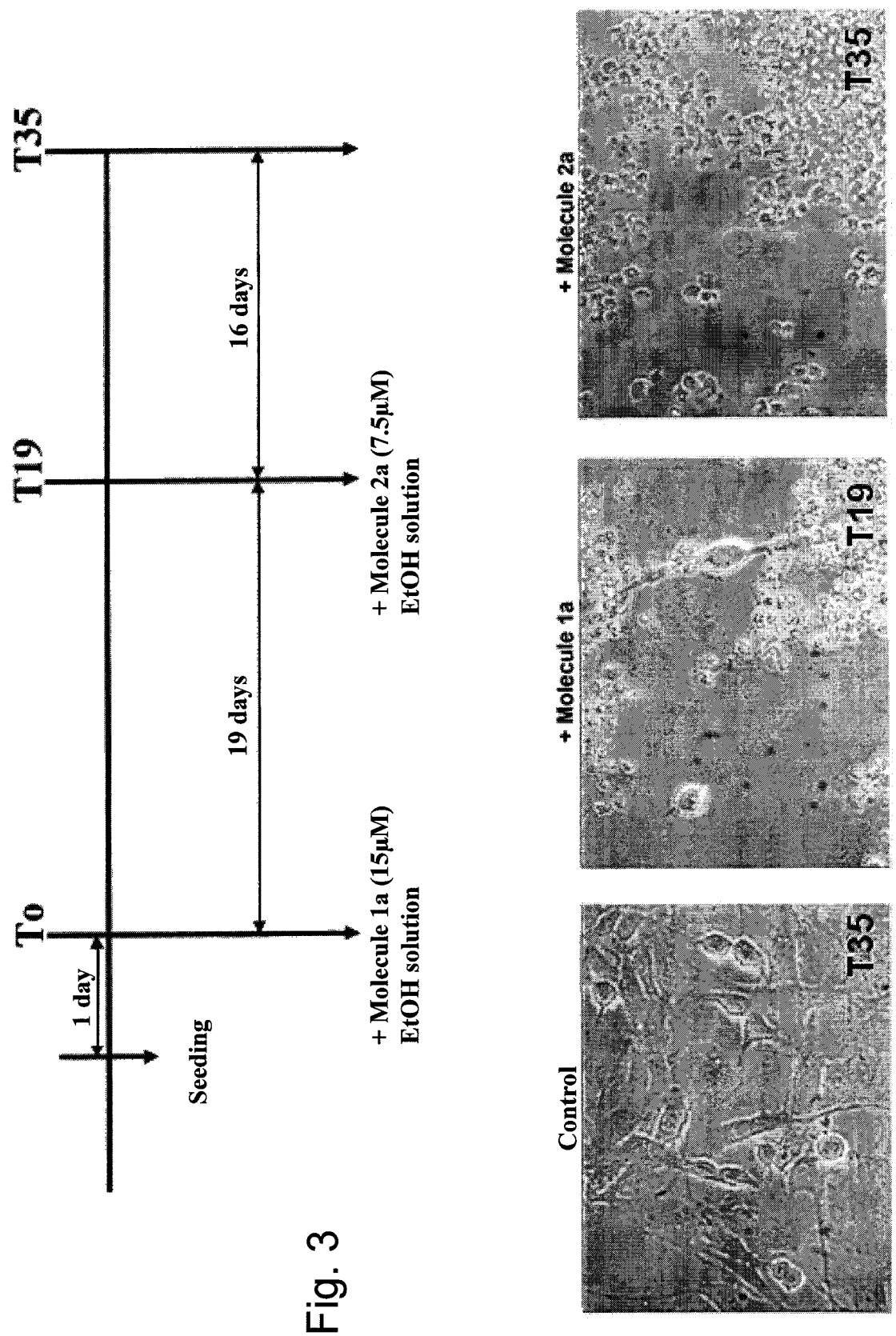
FIG. 3 shows (at magnification 20×10) the appearance of the cultures of C6 cells control at 35 days, and the cultures the cultures of C6 cells in the presence of molecule 1.a, after sequential treatment with molecule 1.a and then molecule 2.a, at 19days and at 35 days.

FIG. 3 (magnification 20×10) shows the appearance of the cultures of C6 cells under the operating conditions mentioned above (section II, A) in the presence of molecule 1.a (Ex.3) or after sequential treatment with molecule 1.a and then molecule 2.a (Ex.5), at 19 days and at 35 days.

The results (Table 1) show that molecule 1.a, in ethanolic form, is cytotoxic, after 19 days of treatment. At 15 µM of 1.a and after 14 days of treatment, the number of cells, the level of proteins and the MTT assay is reduced by 30% and reach 97% reduction, at least, at 19 days. At 19 days of treatment, dose-dependence is also observed for 7.5 and 3.3 µM of 1.a and at 15 µM an increase of the MTT/cell ratio of 20% relative to the control cultures is observed.

In order to remove the residual cells, a sequential treatment was used. The cells are first treated with 15 µM of molecule 1.a and on the 19th day of treatment, molecule 2.a is added at a concentration of 7.5 µM.

No viable cell is observed; only cell "cadavers" adhere to the solid substrate of the cell culture (bottom of the well) as shown in FIG. 3.

To summarize, sequential treatment with molecule 1.a and then molecule 2.a shows complete efficacy against this cell type. The observations indicate an increase in overall respiration of the cells prior to their destruction.

B.2. The Human Model: Anti-GBM Activity "In Vitro" on Cultures of Human Cells (Line U-87 GM)
B.2.1 Definition of the Model "In Vitro" and of Expression of the Results
a) Characterization of the Different Cell Types
The U-87GM cells were cultured under the operating conditions described above (section II, A).

The cultures are made up of two cellular components: a cell layer composed of cells behaving as normal (non-cancerous) cells and cell aggregates composed of GBM type cells.

Figure 4:
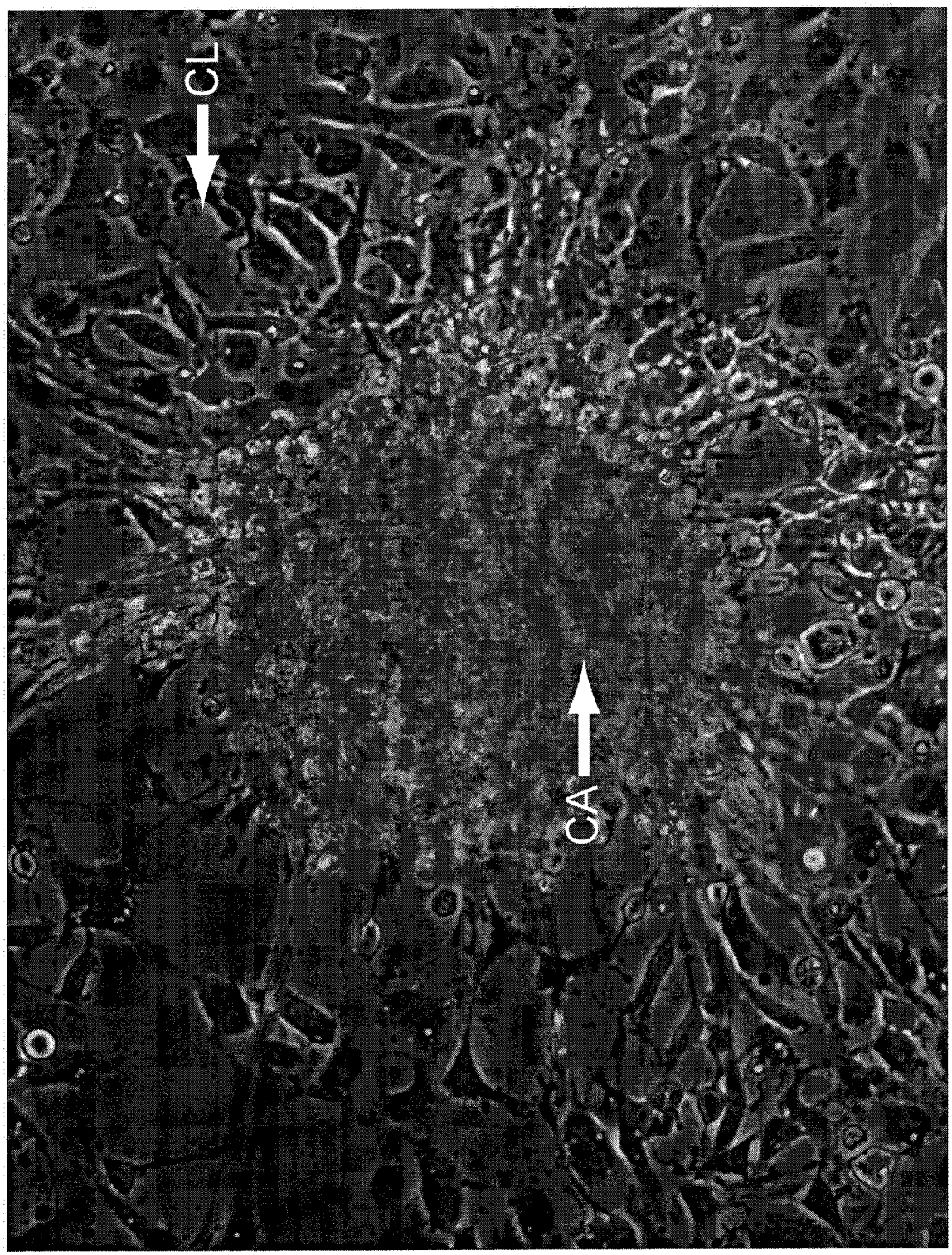
FIG. 4 shows an optical image (10×10) that is characteristic of the U-87GM cell culture with a cell layer (CL) on which cell aggregates of hemispherical shape become fixed.
Figure 5:
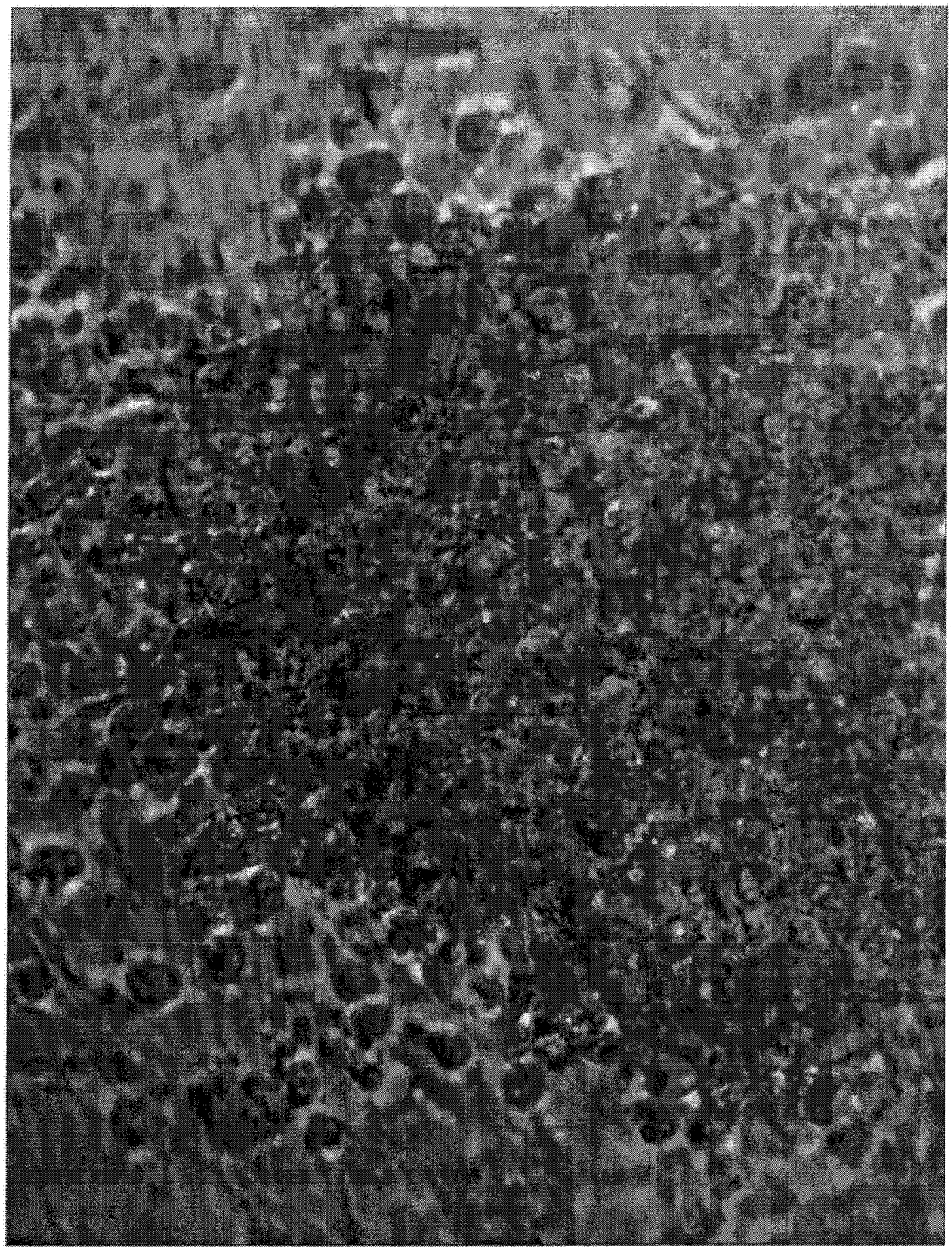
FIG. 5 shows an optical image (20×10) by immunolabelling that that the CD133+ cells (stem cells), described in human GBMs, are located in the cell aggregates and not in the cell layer.
Figure 6:
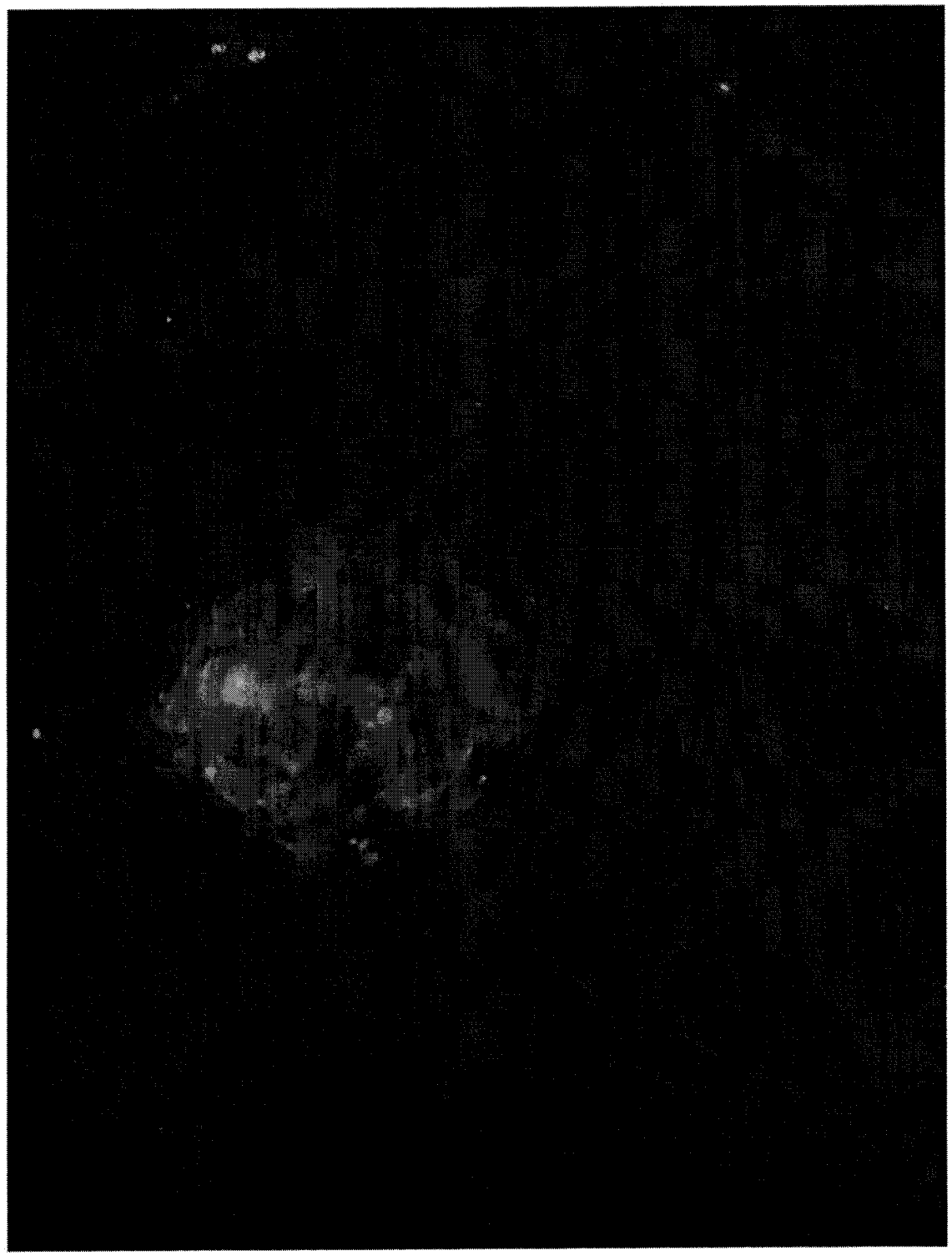
FIGS. 6 and 7 show an optical image (20×10), by immunofluorescence labelling, the presence of GFAP, a marker of normal astrocytes in the cell layer and cell aggregates.
Figure 7:

FIG. 4 shows an optical image (10×10) that is characteristic of the culture. A cell layer (CL) can be seen, on which cell aggregates (CA) of hemispherical shape become fixed. FIG. 5 (20×10) shows, by immunolabelling, that the CD133+ cells (stem cells), described in human GBMs, are located in the cell aggregates and not in the CL. Immunofluorescence labelling shows the presence of GFAP, a marker of normal astrocytes (FIGS. 6 and 7; 20×10) (26) in the CL and CA (FIGS. 6 and 7; 20×10) and of neurofilaments in CL and CA. However, specific labelling of fibroblasts, cells with high potential for multiplication, is only found in the case of CA. Very few IDH1-R132H-positive cells are observed in CL and CA. Conversely, CD31-positive cells are present in CL and CA.

Observation by optical microscopy clearly shows that the cells of the CAs divide very rapidly (doubling time of at most 16 h), whereas the cells making up the CL have a doubling time of 96 h.

These observations justify the cell counting method (cells labelled or not with formazan grains) that has been developed; in fact, counting after trypsinization cannot distinguish between the cells of CL and CA. The images also show that only the CAs have a GBM character (short doubling time, presence of stem cells and fibroblasts). The results obtained are therefore those of the effect of the molecules tested on CA.

b) Expression of the Results
The results are expressed according to the following parameters:
(i) Efficacy of the molecules according to the invention
  Quantification of the residual cells, the stem cells in particular.
  Efficacy of the molecules according to the invention over time
  The culture medium containing the molecules according to the invention is replaced with fresh medium and the "de novo" cell multiplication is examined: no "de novo" multiplication signifies total destruction of the GBM cells, including the stem cells.
(ii) Effect of the molecules on the total respiration of the GBM cells.
(iii) Comparison of the results obtained with the molecules according to the invention with those obtained with 7β-OHCH—C3-ester (control).
B.2.2 Results
Cultures of U87-MG (human) cells were used under the operating conditions mentioned above (section II, A).
The 7beta-OHCH—C3-ester was used as control.

EXAMPLE 8

Study of the Anti-GBM Activity "In Vitro" of Molecule 2.a (Ex.5) in Liposomal Form The results obtained are presented in Table 2 below.

TABLE 2

| Days of treatment | Molecule 2.a (15 µM) in liposomal form | | 7β-OHCH-C3-ester (80 µM) in liposomal form | |
|---|---|---|---|---|
| | Proteins | MTT/cell | Proteins | MTT/cell |
| 6 | 70 | 100 | 70 | 100 |
| 8 | 25 | 140 | 20 | 100 |
| 13 | 15 | 120 | 15 | 100 |
| 15 | 0 | 0 | 15 | 100 |

These results are the mean value of three independent experiments carried out in triplicate. The results are expressed as a percentage relative to the controls.

The observations show that 15 µM of molecule 2.a, in liposomal form, reduces the presence of GBM cells (CA) to zero after 15 days of treatment.

Only the cells with slow division (CL) remain. The effect is not dose-dependent. The 7β-OHCH—C3-ester does not act in ethanolic form on the GBMs (CA) (see also Example 9), and only acts in liposomal form, namely at 80 µM. Its' efficacy is not better, or even decreases, on increasing the dose of 7β-OHCH—C3-ester in liposomal form.

However, if on the 13th day of treatment the culture medium containing the 7β-OHCH—C3-ester is removed and is replaced with a fresh culture medium not containing this drug, cell multiplication is observed, and, in parallel, an increase in the MIT test after two days; this increase is 40%. This is not the case for molecule 2.a: in the absence of this molecule, no cell multiplication is observed.

Table 2 also shows a large increase in MTT/cell (140% relative to the controls) at the time when most of the cells disappear (8 days of treatment). This is not the case for the liposomal 7β-OHCH—C3-ester: even at 80 µM, the MTT/cell ratio does not vary.

This observation shows a different action between the two molecules: the overall cellular respiration increases before massive death of the cells. This is not the case for the 7β-OHCH—C3-ester.

EXAMPLE 9

Study of Anti-GBM Activity "In Vitro" of Molecule 2.b (Ex.6) in Ethanolic Form

The results obtained are presented in Table 3 below.

TABLE 3

|  | Molecule 2.b (30 µM) in ethanolic form | | 7β-OHCH-C3-ester (30 µM) in ethanolic form | |
| --- | --- | --- | --- | --- |
| Days of treatment | Proteins | MTT/cell | Proteins | MTT/cell |
| 4 | 100 | 100 | 100 | 100 |
| 6 | 100 | 100 | 100 | 100 |
| 9 | 90 | 160 | 100 | 100 |
| 15 | 50 | 130 | 100 | 100 |
| 22 | 0 | 0 | 100 | 100 |

These results are the mean value of three independent experiments each carried out in triplicate. The results are expressed as a percentage relative to the controls. Above 30 µM, the 7β-OHCH—C3-ester is no longer soluble in ethanol.

The observations show that molecule 2.b is completely effective at 30 µM in ethanolic form: no GBM cell remains, even after removing the active ingredient. Just as for molecule 2.a, in liposomal form, cellular respiration increases before cell death. This is not the case for the ethanolic 7β-OHCH—C3-ester, no anti-tumour activity is observed.

Moreover, replacement of the culture medium with fresh medium not containing compound 2.b at 22 days does not lead to any cellular multiplication.

EXAMPLE 10

Immunolabelling of the CD133+ Stem Cells with the A/B Peroxidase System

The immunolabelling is carried out as described above (section II, A).

The results obtained are presented in Table 4 below.

TABLE 4

| | CD133+ cells | | |
| --- | --- | --- | --- |
| Days of treatment | Untreated cultures (Controls) | Molecule 2.b (30 µM) in ethanolic form | 7β-OHCH—C3-ester (80 µM) in liposomal form |
| 4 | 100 | 100 | 100 |
| 22 | 100 | 0 | 50 |

These results are the mean value of two independent experiments each carried out in triplicate. The results are expressed as a percentage of CD133 positive cells relative to the controls. These experiments are independent of those described in Examples 8 and 9.

As in the observations described in Tables 2 and 3, 7β-OHCH—C3-ester in liposomal form and molecule 2.b in ethanolic form reduce the level of proteins by 85% and by 100% relative to the untreated control cells.

The results show that the stem cells are completely destroyed by molecule 2.b This is not the case for the 7β-OHCH—C3-ester, even when administered in liposomal form.

Figure 9:
FIG. 9 shows (by immunolabelling of the CD 133+ cells) that the treatment of CD 133+ stem cells with molecule 2.b completely destroys the stem cells, evidenced by their disappearance after 22 days of treatment.
Figure 10:
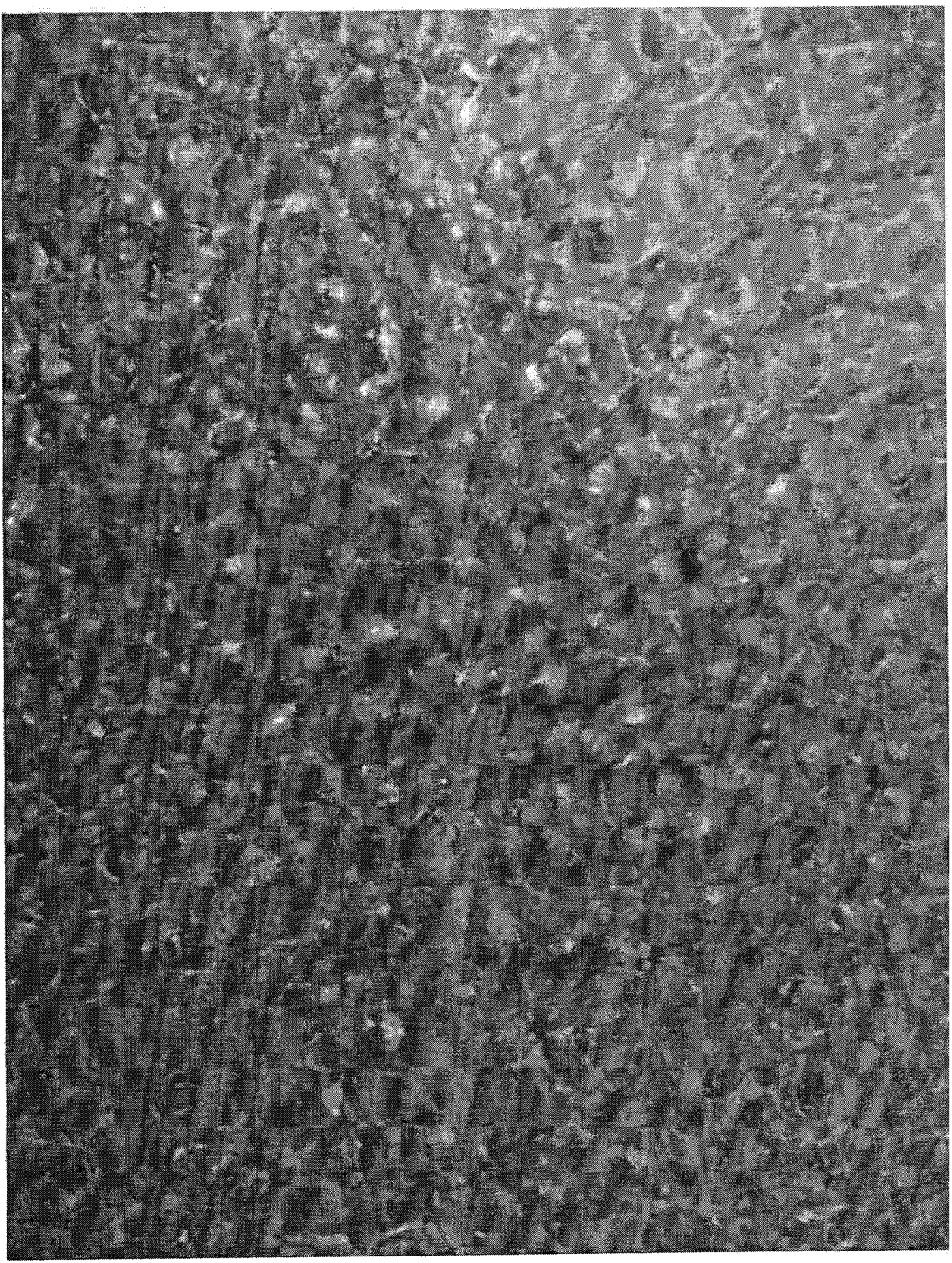
FIG. 10 shows(by immunolabelling of the CD 133+ cells) that treatment of CD 133+ stem cells with the 7beta-OHCH-C3-ester in liposomal form does not completely destroy the CD 133+.

FIG. 9 (immunolabelling of the CD133$^+$ cells) clearly shows their disappearance after 22 days of treatment. This is not the case for the 7β-OHCH—C3-ester in liposomal form (FIG. 10, immunolabelling of the CD133$^+$ cells); in this case, 50% of the CD133$^+$ cells are still present among the residual cells. Replacing the culture medium with fresh medium not containing compound 2.b at 22 days does not lead to the appearance of CD133+ stem cells.

EXAMPLE 11

Study of the Fate of Molecule 2.b (Ex. 6) in Ethanolic Form "In Vitro" in GBMs of Human Origin Extraction and analysis of the lipids from GBM treated with 30 µM of molecule 2.b in ethanolic form does not show the presence of 7beta-OHCH—C3-ester after 24 h or 10 days of treatment, the latter time being that when cell death is initiated. However, 0.12% and 0.18% of molecule 2.b transformed into 7beta-OHCH is observed after 1 day and 10 days of treatment respectively. Control experiments show that these very low levels of 7beta-OHCH do not induce any death of GBMs.

EXAMPLE 12

Study of Toxicity

Toxicity was tested "in vitro" on various normal cell types of human origin.

a) on Astrocytes

The cells used are cells of human origin (ScienCell, USA, ref. 1800), mentioned above (section II, A).

Figure 11:
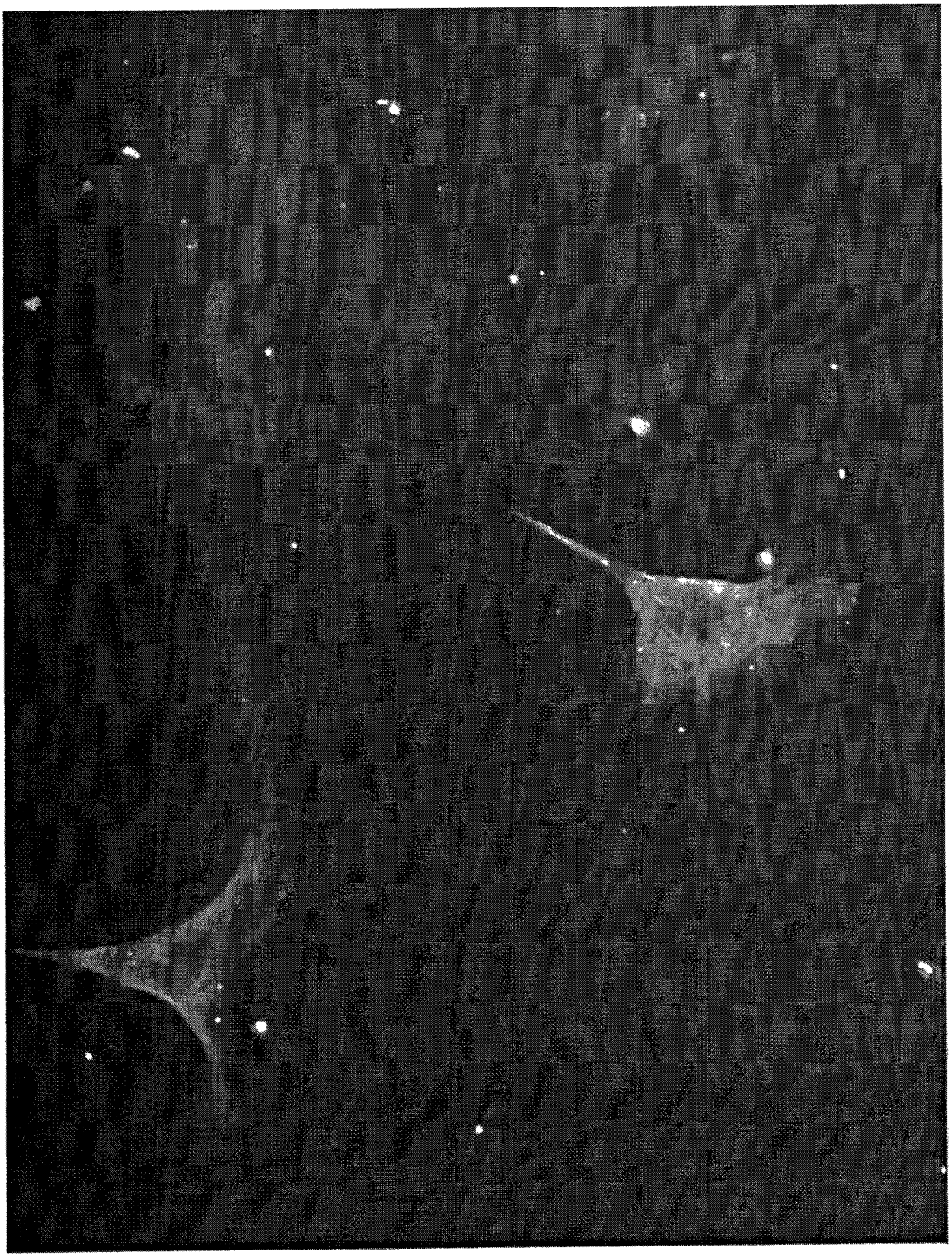
FIG. 11 shows (at magnification×200) the presence of GFAP, which is the standard marker of normal astrocytes.

The astrocyte type is validated by the presence of GFAP, the standard marker of normal astrocytes (FIG. 11; magnification×200).

Molecules 2.a (liposomal form) and 2.b (ethanolic form) are not toxic on primary cultures of normal (non-cancerous) human astrocytes at 30 µM, after 30 days of treatment.

b) on Other Cells

The cells used are liver cells (ScienCell, USA, ref. 50200), kidney cells (ScienCell, USA, ref. 4120), skeletal muscle cells (ScienCell, USA, ref. 3500) and cardiac cells (ScienCell, USA, ref. 6300), of human origin, mentioned above (section II, A).

Molecules 2.a (liposomal form) and 2.b (ethanolic form) are not toxic at 30 µM and after at least 30 days of treatment, on primary cultures of liver cells, kidney cells, skeletal muscle cells and cardiac cells of human origin.

EXAMPLE 13

Study of the Activity of Molecule 2.b (Ex.6) "In Vitro" on Other Cancers

The cancer cells used are from liver (ref. ATCC-HB-8065), prostate (ref. ATCC-HTB-81), breast (ref. ATCC-HTB-19) cancer cells, and from colon cancer cells (ECACC-HT29/219) of human origin, mentioned above.

At 30 µM and in ethanolic form, molecule 2.b shows no effect on cellular division and respiration of liver, prostate or breast cancer cells of human origin.

At 15 µM, molecule 2.b in improved liposomal form is not toxic to colon cancer cells.

EXAMPLE 14

Study of the Activity of Molecule 2.b in Improved Liposomal Form "In Vitro" on Chronic Myelomonocytic Leukaemia (CMML)

The white blood cells are isolated from a blood sample collected from a patient suffering from CMML. The cells are treated once with 10 µM of molecule 2.b in improved liposomal form 24 hours after culturing by seeding on a feed layer (17).

Figure 12:
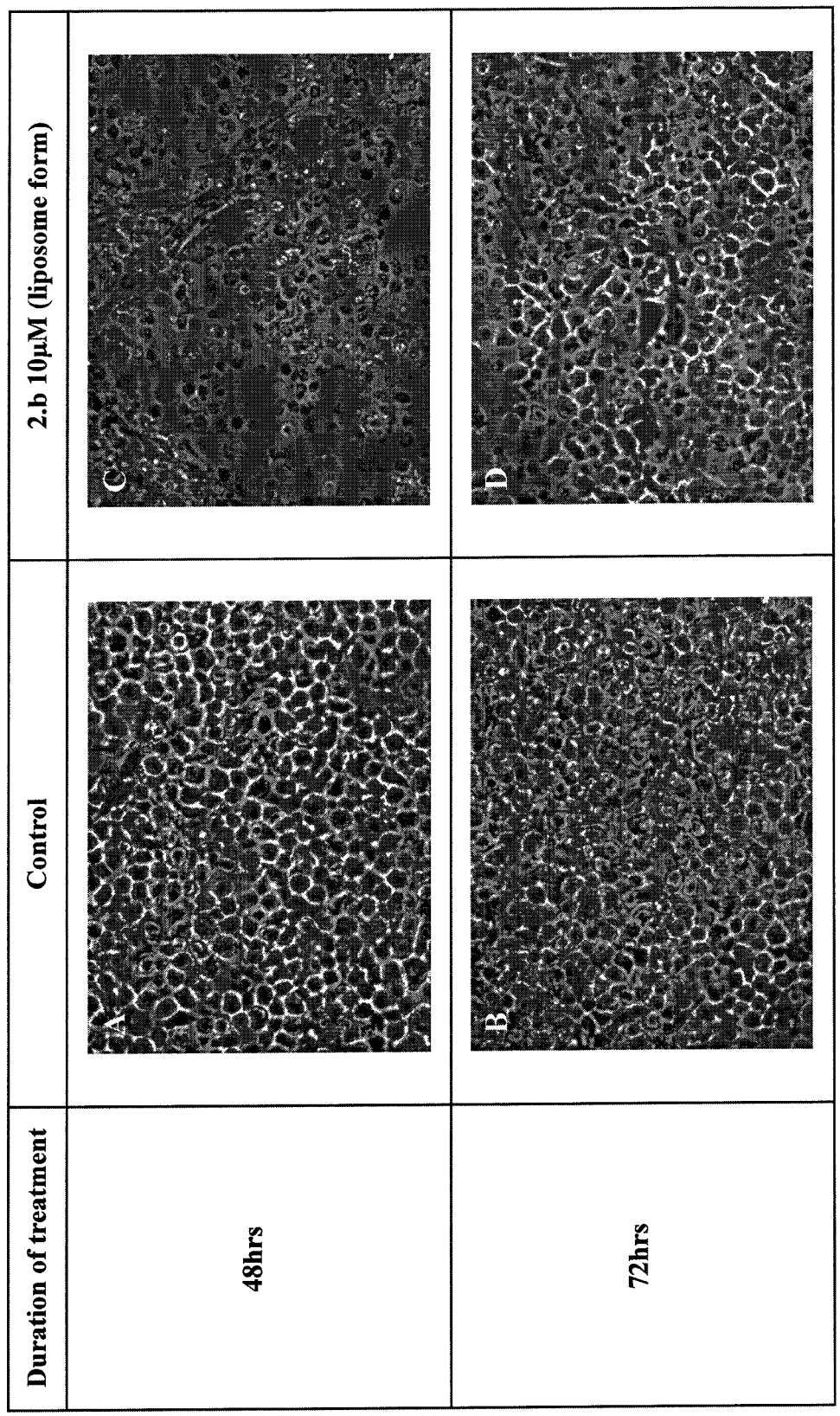
FIG. 12 shows the results (in photographs at magnification 20×10) of white blood cells from a patient suffering from Chronic Myelomonocytic Leukaemia treated with molecule 2.b.

The results are shown in the photographs in FIG. 12 (magnification 20×10).

The controls are cells treated with empty liposomes: the upper left hand photograph marked with the letter A was taken after 48 h of treatment and the lower left hand photograph with the letter B after 72 h of treatment.

For the cells treated with 2.b, the upper right hand photograph marked with the letter C was taken after 48 h of treatment and the lower right hand photograph with the letter D after 72 h of treatment.

The results show a remarkable effect of molecule 2.b after 72 h of treatment. Cell multiplication is slowed considerably relative to the control and many cells with a necrotic appearance are observed.

EXAMPLE 15

Study of the Activity of Molecules 1.b and 2.b "In Vitro" on Human Neuroblastomas (ATCC-CRL-2266)

The neuroblastomas were treated with empty liposomes (controls) or with liposomes containing molecule 1.b or 2.b, 24 h after starting the culture. The cells are treated once with 22 µM of molecule 1.b or 22 µM of molecule 2.b. The liposomal form is concentrated.

The results are shown in the photographs in FIG. 13 (magnification 10×10).

For the control cells, the upper left hand photograph marked with the letter A was taken after 7 days of treatment; the lower left hand photograph marked with the letter B was taken after 28 days of treatment.

For the cells treated with the concentrated liposomal molecule 1.b, the photograph marked with the letter C (in the middle, at the top) was taken after 7 days of treatment and the photograph marked with the letter D (in the middle, at the bottom) after 28 days of treatment. For the cells treated with the concentrated liposomal molecule 2.b, the upper right hand photograph marked with the letter E was taken after 7 days of treatment.

The results show remarkable activity of molecule 2.b relative to molecule 1.b. After 28 days of treatment, molecule 1.b is toxic to almost all the cells, compared to the control cells. For molecule 2.b, a radical toxic effect is already observed after 7 days of treatment; no viable cell is observed.

EXAMPLE 16

Study of the Inhibition of the Activity of LDH Extracted from Human GBH "In Vitro" (U87-MG Lines) by Molecule 2.b The objective of these experiments was to demonstrate the potential for inhibition of the enzymatic activity of LDH of the series 2 molecules. The study was carried out with molecule 2.b and its inhibitory potential was tested on LDH from *Lactobacillus leichmannii* (LL) and partially purified LDH from human GBM lines (U87-MG) as described above in the section "A/ PROTOCOLS 6)".

The activity of LDH is detected by the "in gel assay" technique on IEF electrophoresis gels, which were described in the section "A/ PROTOCOLS 6)" (25); the precision of this technique is 0.2 unit of pH. The activity of LDH is detected by a dark blue precipitate, of the formazan type, the site where LDH activity is located.

Figure 14:
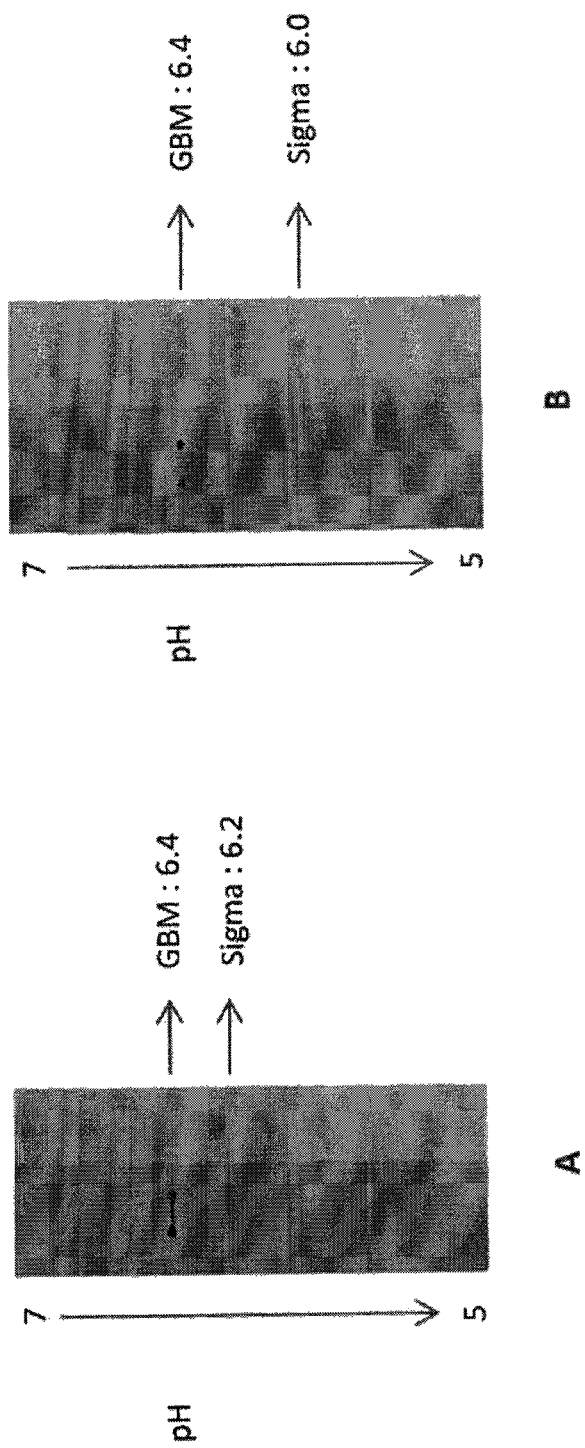
FIG. 14 (A) shows LDH activity for LDH LL at pHi 6.2 and for LDH GBM at pHi 6.4.

FIG. 14 (A) shows LDH activity for LDH LL at pHi 6.2 and for LDH GBM at pHi 6.4.

The results show that the addition of oxamate, in aqueous form (18 mM), or of molecule 2.b, in ethanolic form (36 mM), inhibits the enzymatic activity of LDH LL almost completely and that of LDH GBM (B) partially.

Figure 8:
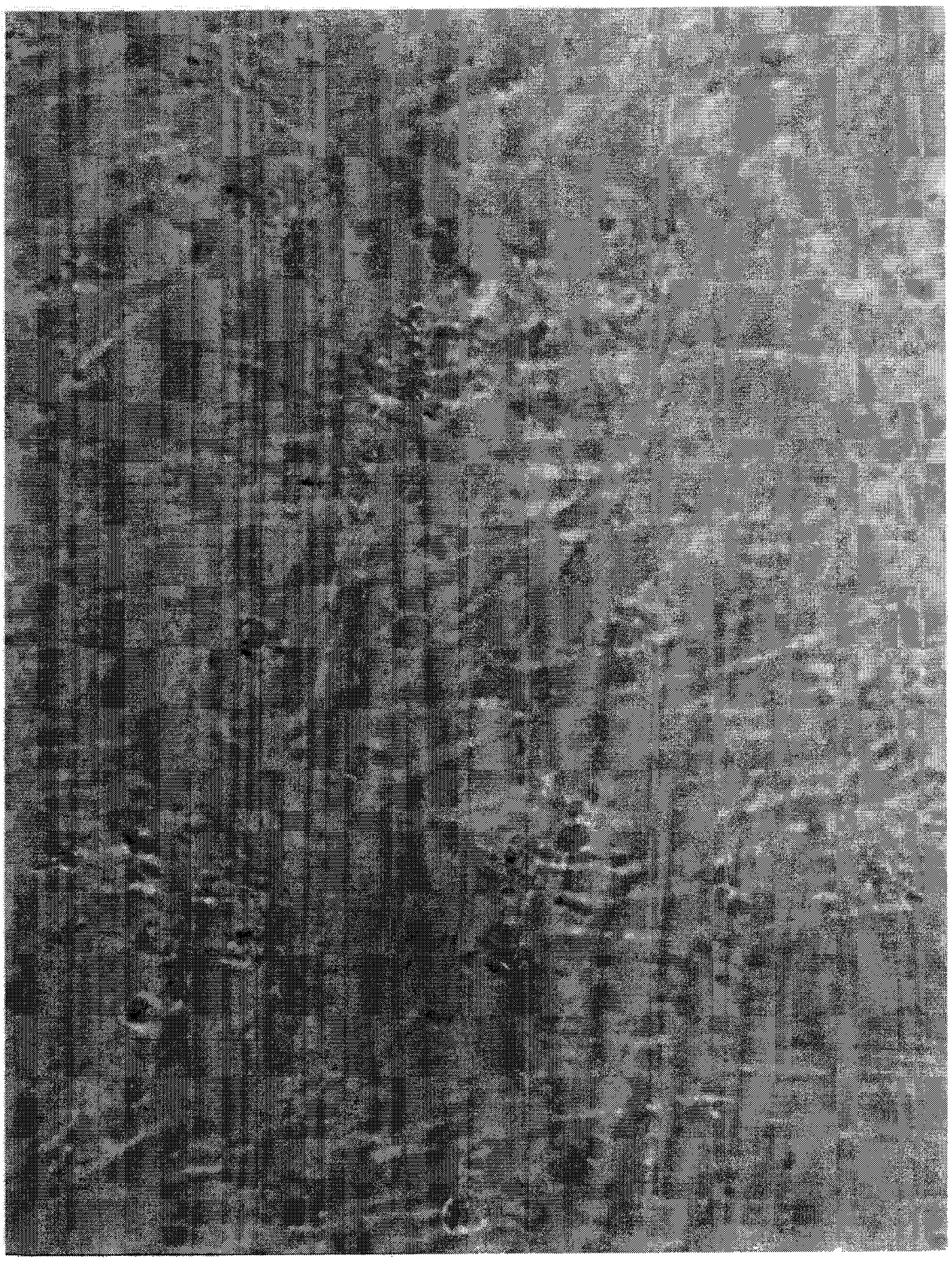

The potential for inhibition of the enzymatic activity of LDH GBM by molecule 2.b combined with the increase in MTT staining before cell death of GBM (Tables 2 and 3; FIGS. 8 and 9) validates the hypothesis of the mechanism of action of the compounds of formula (I): the molecules of the invention would inhibit the activity of LDH and, consequently, would cause a burst of mitochondrial respiration.

BIBLIOGRAPHY

1. Kando T, Setoguchi T, Taga T. PNAS. 2004, 101: 781-786.
2. Zhou Y, Zhou Y, Shingu T, Feng L, Chen Z, Ogasawara M, Keating M J. J. Biol. Chem. 2011, 286: 32843-32853).
3. Warburg O. Biochemische Zeitschrift. 1923, 142: 317-333.
4 Tennant D A, Duran R V, Gottlieb E. Nature Reviews Cancer. 2010, 10: 267-277.

5. Cheng K P, Nagano H, Bang L, Ourisson G, Beck J P. Journal of Chemistry Research (M). 1977, 217:2501-2521.
6. Carvalho J F S, Cruz Silva M M, Moreira J N, Simoes S, Sa e Melo M L. Journal of Medicinal Chemistry. 2011, 54: 6375-6393.
7. Kupferberg A, Teller G, Behr P, Leray C, Urban P F, Vincendon G, Mersel M. Biochim Biophys Acta. 1989, 1013: 231-23.
8. Kupferberg A, Behr P, Mersel M. Biochim Biophys Acta. 1990, 1046: 106-109.
9. Adamczyck M, Scherrer E, Kupferberg A, Malviya A N, Mersel M. Journal of Neuroscience Research. 1988, 53:38-50.
10. Werthle M, Bochelen D, Adamczyck M, Kupferberg A, Poulet P, Chambron J, Lutz P, Privat A, Mersel M. Cancer Research. 1994, 54: 998-1003.
11. Clarion L, Schindler M, de Weille J, Lolmède K, Laroche-Clary A, Uro-Coste E, Robert J, Mersel M, Bakalara N.
12. El Kihel L et al. J. Org. Chem. 2002: 4075-4078.
13. Yusuf R Z, Wang Y H, Sccaden D T. Nature Medicine 2012, 18: 865-867.
14. Langman J. Embryologie Médicale [Medical Embryology], Publ. Masson 1974, 66-70. Biochemical Pharmacology. 2012, 83: 37-46.
15. Manford K, Patterson J R. Methods in Enzymology. 1979, 58: 150.
16. Benda P, Lightbody J, Sato G, Levine L, Sweet W. Science. 1968, 161: 370-371.
17. Rouleau C, Mersel M, de Weille J, Rakotoarivelo C, Fabre C, Privat A, Langley K, Petite D. J of Neurosc. 2000, 87: 50-60.
18. Rakotoarivelo C, Adamczyck M, Desgeorges M, Langley K, Lorentz J G, Mann A, Ricard D, Scherrer E, Privat A, Mersel M. Anticancer Res. 2006, 26: 2053-2062.
19. Folch J, Lees M, Sloane-Stanley G H. J Biol. Chem. 1957, 226: 5497-5509.
20. Kates M. Techniques of Lipidology, Work T S and Work E editors Elsevier Publishing 1975, 368-369.
21. Balss J, Meyer J, Mueller W, Korshunov A, Hartmann C, Von Deimling A. Acta Neuropathol. 2008, 116: 597-602.
22. Bogen S A, Baldwin H S, Watkins S C, Albelda S M, Abbas A K. Am J. Pathol. 1992, 141: 843-854.
23. Schurr A, Payne R S. Neuroscience 2007, 147: 613-619.
24. Scientific Committee. Recommandations pour la mesure de la concentration catalytique de la lactate déhydrogenase dans le sérum humain à 30° C. [Recommendations for measuring the catalytic concentration of lactate dehydrogenase in human serum at 30° C.]. Ann Biol Clin 1982, 40: 87-164.
25. Seger J., Lucotte G. La Pratique de l'électrophorese appliquée à la détection des polymorphismes humains. [The electrophoresis technique applied to the detection of human polymorphisms]. Masson Ed., 1982, 68-69
26. Sensenbrenner M, Devilliers G, Bock E, Porte A. Differentiation, 1980, 17: 51-61.

The invention claimed is:

1. A compound of formula (I) having a 7beta-hydroxycholesterol basic structure

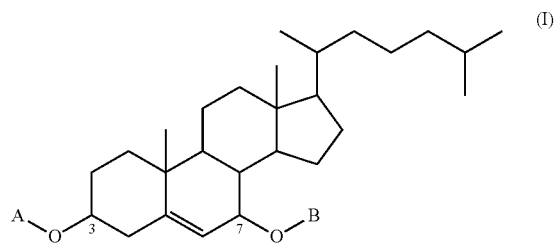

in which

A represents:
- an —(R$_1$)$_n$— group in which R$_1$ is an amino acid residue, n=1 or 2, each R$_1$ being identical or different, and the N-terminal end of said amino acid is optionally substituted with an arylalkoxycarbonyl group ; or
- a —C(O)—R$_6$ group in which R$_6$ is a saturated heterocycle comprising 5 to 14 members and including 1 or 2heteroatoms, unsubstituted or substituted with at least one linear or branched C$_1$-C$_6$ alkyl B represents:
- a —C(O)—R$_7$ group in which R$_7$ is a C$_1$-C$_{12}$alkyl, linear or branched; or R$_7$ represents OR$_8$, in which R$_8$ is a linear or branched, C$_1$-C$_{12}$ alkyl.

2. The compound of formula (I) according to claim 1, in which at least one of the following conditions is fulfilled:

A represents an —(R$_1$)$_n$— group in which R$_1$ is an amino acid residue and n=1 or 2, each R$_1$ being identical or different, and the N-terminal end of said amino acid is optionally substituted with an arylalkoxycarbonyl gorup;

A represents an —(R$_1$)$_n$— group in which R$_1$ is an amino acid residue, n=1 or 2, each R$_1$ being identical or different, and the N-terminal end of said amino acid is substituted with an arylalkoxycarbonyl group or A represents an alanyl radical linked to a glycinyl radical, optionally substituted on its N-terminal end with an arylalkoxycarbonyl group.

3. The compound of formula (I) according to claim 1, in which A represents a —C(O)—R$_6$ group in which R$_6$ is a 2,2-dimethyl-1,3-dioxolane group.

4. The compound of formula (I) according to claim 1, in which B represents an acyl group —C(O)—R$_7$ in which R$_7$ is a C$_1$-C$_6$ alkyl group, or an alkoxycarbonyl group C(O)-R$_7$ in which R$_7$ is OR$_8$, and R$_8$ is a C$_1$-C$_6$ alkyl group.

5. A compound of formula (I),

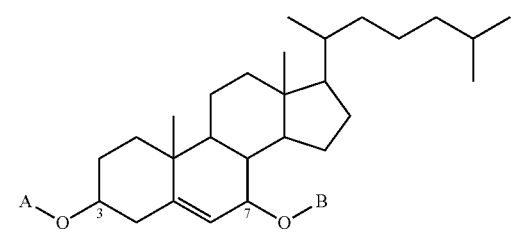

as defined by claim 1, wherein the compound is selected from the group consisting of:

7-((tert-butoxycarbonyl)oxy)-10,13-dimethyl-17-(6-methylheptan-2-yl) -2,3,4,7,8,9,10,11,12,13,14,15,16,17-tetradecahydro-1H-cyclopenta[a]phenanthren -3-yl 2-(2-(((benzyloxy)carbonyl)amino)-acetamido)propanoate (molecule 1.a);

7-acetoxy-10,13-dimethyl-17-(6-methylheptan-2-yl)-2,3,4,7,8,9,10,11,12,13,14,15,16,17-tetradecahydro-1H -cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H -cyclopenta[a]-phenanthren-3-yl 2,2-dimethyl-1,3-dioxolane-4 -carboxylate (molecule 2.b).

6. The compound of formula (I) according to claim 1, in which A represents an —$(R_1)_n$— group in which $R_1$ is an amino acid residue, n=1 or 2, each $R_1$ being identical or different, and the N-terminal end of said amino acid is substituted with a benzyloxycarbonyl group.

7. The compound of formula (I) according to claim 1, in which A represents an alanyl radical linked to a glycinyl radical, optionally substituted on its N-terminal end with a benzyloxycarbonyl group.

8. The compound of formula (I) according to claim 1, in which B represents a —C(O)—$R_7$ group in which $R_7$ is a linear or branched $C_1$-$C_6$ alkyl.

9. The compound of formula (I) according to claim 1, in which B represents a —C(O)—$R_7$ group in which $R_7$ represents $OR_8$, in which $R_8$ is a linear or branched $C_1$-$C_6$ alkyl.

10. The compound of formula (I) according to claim 1, in which B represents acetyl or a tert-butoxycarbonyl group.

11. The compound of formula (I) according to claim 1, in which B which B represents an acyl group —C(O)—$R_7$ in which $R_7$ is methyl.

12. The compound of formula (I) according to claim 1, in which B represents an alkoxycarbonyl group —C(O)—$R_7$ in which $R_7$ represents $OR_8$ and $R_8$ is a tert-butyl group.

13. A pharmaceutical composition comprising at least one compound of formula (I) according to claim 1 and a pharmaceutically acceptable vehicle.

14. The pharmaceutical composition according to claim 13, wherein the composition consists of a liposome comprising at least one compound of formula (I), alone or in combination with another active ingredient.

15. The pharmaceutical composition according to claim 13, wherein the composition consists of an alcoholic solution comprising at least one compound of formula (I), alone or in combination with another active ingredient.

16. The pharmaceutical composition according to claim 13, wherein the composition is suitable for administration by oral route.

17. The pharmaceutical composition according to claim 16, wherein the composition is in a form selected from the group consisting of tablets, capsules, powders, granules, solutions, emulsions, oral suspensions, drops, syrups, complexes of compounds of formula (I) with biliary salts and combinations of compounds of formula (I) with phospholipids, in liposomal or non-liposomal form.

18. The pharmaceutical composition according to claim 13, wherein said compound of formula (I) is used as the only active ingredient, or in combination with an anti-cancer agent.

19. The pharmaceutical composition according to claim 13, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.a);

7-acetoxy-10,13-dimethyl-17-(6-methylheptan-2-yl) -2,3,4,7,8,9,10,11,12,13,14,15,16,17-tetradecahydro-1H -cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H -cyclopenta[a]-phenanthren-3-yl 2,2-dimethyl-1,3-dioxolane-4-carboxylate (molecule 2.b).

20. A pharmaceutical composition, comprising at least one compound of formula (I) and a pharmaceutically acceptable vehicle, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.a);

7-acetoxy-10,13-dimethyl-17-(6-methylheptan-2-yl) -2,3,4,7,8,9,10,11,12,13,14,15,16,17-tetradecahydro-1H -cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H -cyclopenta[a]-phenanthren-3-yl 2,2-dimethyl-1,3-dioxolane-4-carboxylate (molecule 2.b), and wherein the composition is in a form suitable for administration by oral route, the form being selected from the group consisting of tablets, capsules, powders, granules, solutions, emulsions, oral suspensions, drops, and syrups.

21. The pharmaceutical composition according to claim 20, wherein the compound is part of a complex with a biliary salt or the compound is combined with phospholipids, in liposomal or non-liposomal form.

22. A method of treating glioblastoma multiforme, comprising administering to a subject in need thereof an effective amount of a compound of formula (I) according to claim 1.

23. The method according to claim 22, wherein said administering is a sequential treatment comprising at least one step of administering a first compound of formula (I) and at least one step of administering a second compound of formula (I), different from the first.

24. The method of treating glioblastoma multiforme according to claim 22, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1. a);

7-acetoxy-10,13-dimethyl-17-(6-methylheptan-2-yl) -2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H-cyclopenta[a]-phenanthren-3-yl 2,2-dimethyl-1,3-dioxolane-4-carboxylate (molecule 2.b).

25. A method of treating malignant haemopathies, comprising administering to a subject in need thereof an effective amount of a compound of formula (I) according to claim 1.

26. The method according to claim 25, wherein the malignant haemopathies are of the myeloid type.

27. The method according to claim 25, wherein the malignant haemopathies are lymphomas.

28. The method of treating malignant haemopathies according to claim 25, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.a);

7-acetoxy-10,13-dimethyl-17-(6-methylheptan-2-yl) -2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H-cyclopenta[a]-phenanthren-3-yl 2,2-dimethyl-1,3-dioxolane-4-carboxylate (molecule 2.b).

29. The method according to claim 28, wherein the malignant haemopathies develop from myeloid cells.

30. The method according to claim 28, wherein the malignant haemopathies are lymphomas.

31. A method of treating neuroblastomas, comprising administering to a subject in need thereof an effective amount of a compound of formula (I) according to claim 1.

32. The method of treating neuroblastomas according to claim 31, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.a);

7-acetoxy-10,13-dimethyl-17-(6-methylheptan-2-yl) -2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H-cyclopenta[a]-phenanthren-3-yl 2,2-dimethyl-1,3-dioxolane-4-carboxylate (molecule 2.b).

33. A method of treating melanomas, comprising administering to a subject in need thereof an effective amount of a compound of formula (I) according to claim 1.

34. A method for the preparation of a compound of formula (I) according to claim 1, comprising the following steps:

protecting the hydroxyl function in position 3 of cholesterol with a protective group, introducing a ketone function in position 7, reducing the ketone function to a hydroxyl function, introducing a protective group on the hydroxyl function in position 7, corresponding to the B group, deprotecting the hydroxyl function in position 3, and substituting the hydroxyl function in position 3 with the A group.

35. The method of treating melanomas according to claim 33, wherein the compound is selected from the group consisting of:

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.a);

7-acetoxy-10,13-dimethyl-17-(6-methylheptan-2-yl) -2,3,4,7,8,9,10,11,12,13,14,15,16,17-tetradecahydro-1H-cyclopenta[a]phenanthren-3-yl 2-(2-(((benzyloxy)carbonyl)amino)-acetamido)propanoate (molecule 1.b);

7-((tert-butoxycarbonyl)oxy)-10,13-dimethyl-17-(6-methylheptan-2-yl)-2,3,4,7,8,9,10,11,12,13,14,15,16,17-tetradecahydro-1H-cyclopenta[a]phenanthren-3-yl 2,2-dimethyl -1,3-dioxolane-4-carboxylate (molecule 2.a); and 7-acetoxy-10,13-dimethyl-17-(6-methylheptan-2-yl) -2,3,4,7,8,9,10,11,12,13,14,15,16,17-tetradecahydro-1H-cyclopenta[a]-phenanthren-3-yl 2,2-dimethyl-1,3-dioxolane-4-carboxylate (molecule 2.b).

\* \* \* \* \*